US008346525B2

(12) United States Patent (10) Patent No.: US 8,346,525 B2
Chen et al. (45) **Date of Patent: *Jan. 1, 2013**

(54) METHODS OF MODELING PHYSICAL PROPERTIES OF CHEMICAL MIXTURES AND ARTICLES OF USE

(75) Inventors: Chau-Chyun Chen, Lexington, MA (US); Yuhua Song, Somerville, MA (US)

(73) Assignee: Aspen Technology, Inc., Burlington, MA (US)

( * ) Notice: Subject to any disclaimer, the term of this patent is extended or adjusted under 35 U.S.C. 154(b) by 216 days.

This patent is subject to a terminal disclaimer.

(21) Appl. No.: 12/655,988

(22) Filed: Jan. 11, 2010

(65) Prior Publication Data

US 2010/0114542 A1 May 6, 2010

Related U.S. Application Data

(62) Division of application No. 10/785,925, filed on Feb. 24, 2004, now Pat. No. 7,672,826.

(51) Int. Cl.
*G06G 7/58* (2006.01)
*G06G 7/48* (2006.01)
*G01N 33/48* (2006.01)

(52) U.S. Cl. ............................... 703/12; 703/11; 702/19

(58) Field of Classification Search ........................ None
See application file for complete search history.

(56) References Cited

U.S. PATENT DOCUMENTS

| 5,687,090 | A  | 11/1997 | Chen et al. |
| 6,311,093 | B1 | 10/2001 | Brown |
| 6,311,095 | B1 | 10/2001 | Brown |
| 6,662,061 | B1 | 12/2003 | Brown |
| 6,766,817 | B2 | 7/2004  | Dias da Silva |
| 6,918,404 | B2 | 7/2005  | Dias da Silva |
| 7,066,586 | B2 | 6/2006  | Dias da Silva |
| 2005/0187748 | A1 | 8/2005 | Chen et al. |

FOREIGN PATENT DOCUMENTS

EP 0463694 A2 1/1992

OTHER PUBLICATIONS van de Waterbeemd, H., and Gifford, E., "Admet in Silico Modelling: Towards Prediction Paradise?", Nature Publishing Group, Mar. 2003, vol. 2: 192-204.
Chen, C-C., et al., "Segment-Based Excess Gibbs Energy Model for Aqueous Organic Electrolytes", AIChE Journal, Nov. 2001, vol. 47, No. 11, 2593-2602.
Chen, C-C., "Molecular Thermodynamic Model for Gibbs Energy of Mixing of Nonionic Surfactant Solutions", AIChE Journal, Nov. 1996, vol. 42, No. 11, 3231-3240.
Chen, C-C., and Mathias, P.M., "Applied Thermodynamics for Process Modeling", AIChE Journal, Feb. 2002, vol. 48, No. 2, 194-200.
Chen, C-C., "A Segment-Based Local Composition Model for the Gibbs Energy or Polymer Solutions", Fluid Phase Equilibria, vol. 83 (1993), 301-312.

Ahamed, T., et al., "A Generalized Approach to Thermodynamic Properties of Biomolecules for Use in Bioseparation Process Design," *Fluid Phase Equilibria*, 241: 268-282 (2006).
Anderko A., et al., "Electrolyte Solutions: from thermodynamic and transport property models to the simulation of industrial processes," *Fluid Phase Equilibria*, 194-197:123-142 (2002).
Barra, J., et al., "Proposition of Group Molar Constants for Sodium to Calculate the Partial Solubility Parameters of Sodium Salts Using the van Krevelen Group Contribution Method," *European Journal of Pharmaceutical Sciences*, 10:153-161 (2000).
Beerbower, A., et al., "Expanded Solubility Parameter Approach 1: Naphthalene and Benzoic Acid in Individual Solvents," *Journal of Pharmaceutical Sciences*, 73(2):179-188 (1984).
Bustamante, P., et al., "The Modified Extended Hansen Method to Determine Partial Solubility Parameters of Drugs Containing a Single Hydrogen Bonding Group and Their Sodium Derivatives: Benzoic Acid/Na and Ibuprofen/Na," *International Journal of Pharmaceutics*, 194:117-124 (2000).
Chen, C-C., et al., "Local Composition Model for Excess Gibbs Energy of Electrolyte Systems", *AIChE Journal*, 28(4):588-596 (1982).
Chen, C-C., et al., "Use of Hydration and Dissociation Chemistries With the Electrolyte-NRTL Model," *AIChE Journal*, 45(7): 1576-1586 (1999).
Chen, C. C., and Song, Y., "Solubility Modeling with a Nonrandom Two-Liquid Segment Activity Coefficient Model," *Ind. Eng. Chem. Res*, 43(26):8354-8362 (2004).
Chen, C. C., and Song, Y., "Generalized Electrolyte-NRTL Model for Mixed-Solvent Electrolyte Systems," *AIChE Journal*, 50(8):1928-1941 (2004).
Chen, C.-C. and Song Y., "Extension of Nonrandom Two-Liquid Segment Activity Coefficient Model for Electrolytes," *Ind. Eng. Chem. Res.*, 44(23): 8909-8921 (2005).
Chen, C.-C and Crafts, P.A., "Correlation and Prediction of Drug Molecule Solubility in Mixed Solvent Systems with the Nonrandom Two-Liquid Segment Activity Coefficient (NRTL-SAC) Model," *Md. Eng. Chem. Res.*, 45: 4816-4824 (2006).
Frank, T. C., et al., "Quickly Screen Solvents for Organic Solids," *Chemical Engineering Progress*, pp. 41-66 (1999).
Fredenslund, A., et al., "Group-Contribution Estimation of Activity Coefficients in Nonideal Liquid Mixtures," *AIChE Journal*, 21(6): 1086-1099 (1975).
Gracin, S. and Rasmuson, A. C., "Solubility of Phenylacetic Acid, p-Hydroxyphenylacetic Acid, p-Aminophenylacetic Acid, p-Hydroxybenzoic Acid, and Ibuprofen in Pure Solvents," *J Chem. Eng. Data*, 47:1379-1383 (2002).
Hansen, C. M., "Hansen Solubility Parameters A User's Handbook," *CRC Press* (2000).
Miller, J.M. Chromatography, Concepts and Contrasts. 2nd ed. New Jersey: Wiley-Interscience Publication, John Wiley & Sons, Inc., 2005.
Park, J.H., et al., "UNIFAC Model as a Heuristic Guide for Estimating Retention in Chromatography," *J. of Chromatography*, 586: 1-9 (1991).

(Continued)

*Primary Examiner* — Eric S DeJong
(74) *Attorney, Agent, or Firm* — Hamilton, Brook, Smith & Reynolds, P.C.

(57) ABSTRACT

Included are methods for modeling at least one physical property of a mixture of at least two chemical species. One or more chemical species of the mixture are approximated or represented by at least one conceptual segment. The conceptual segments are then used to compute at least one physical property of the mixture. An analysis of the computed physical properties forms a model of at least one physical property of the mixture. Also included are computer program products and computer systems for implementing the modeling methods.

15 Claims, 20 Drawing Sheets

OTHER PUBLICATIONS

Park, J.H., et al., "UNIFAC Model as a Heuristic Guide for Estimating Retention in Reversed-Phased Liquid Chromatography," *J. of Chromatography A*, 656: 69 (1993).

Pitzer, K. S., "Electrolytes. From Dilute Solutions to Fused Salts," *Journal of the American Chemical Society*, 102(9):2902-2906 (1980).

Pitzer, K. S., "Thermodynamics of Electrolytes. I. Theoretical Basis and General Equations," *The Journal of Physical Chemistry*, 77(2):267-277 (1973).

Rashin, A. A. and Honig, B., "Reevaluation of the Born Model of Ion Hydration," *J. Phys. Chem.*, 89 (26):5588-5593 (1985).

Robinson, R. A., D.Sc., Ph.D., F.R.I.C., et al., "Electrolyte Solutions The Measurement and Interpretation of Conductance, Chemical Potential and Diffusion in Solutions of Simple Electrolytes," *Butterworths Scientific Publications Second Edition* (1959).

Synder, L.R., et al. Practical HPLC Method Development. 2nd ed. New Jersey: Wiley-Interscience Publication, John Wiley & Sons, Inc., 1997.

Tung, H.-H., et al., "Prediction of Pharmaceuticals Solubility via NRTL-SAC and Cosmo," *VDI Berichte*, 1901(1): 271-278 (2005).

Wang, et al., "A speciation-based model for mixed-solvent electrolyte systems," *Fluid Phase Equilibria*, 203(1-2): 141-176 (2002).

Wilczek-Vera, Grazyna, et al., "On the Activity of Ions and the Junction Potential: Revised Values for All Data," *AIChE Journal*, 50(2):445-462 (2004).

Lipinski, et al., "Experimental and computational approaches to estimate solubility and permeability in drug discovery and development settings," Advanced Drug Delivery Reviews, 23: 3-25 (1997) (No month available).

METHODS OF MODELING PHYSICAL PROPERTIES OF CHEMICAL MIXTURES AND ARTICLES OF USE

RELATED APPLICATION

This application is a divisional of U.S. application Ser. No. 10/785,925, filed Feb. 24, 2004, issued as U.S. Pat. No. 7,672,826 on Mar. 2, 2010. The entire teachings of the above application are incorporated herein by reference.

BACKGROUND OF THE INVENTION

Modeling physical properties of chemical mixtures is an important task in many industries and processes. Specifically, for many processes, accurate modeling of physical properties for various mixtures is crucial for such areas as process design and process control applications. For example, modeling physical properties of chemical mixtures is often useful when selecting suitable solvents for use in chemical processes.

Solvent selection is an important task in the chemical synthesis and recipe development phase of the pharmaceutical and agricultural chemical industries. The choice of solvent can have a direct impact on reaction rates, extraction efficiency, crystallization yield and productivity, etc. Improved solvent selection brings benefits, such as faster product separation and purification, reduced solvent emission and less waste, lower overall costs, and improved production processes.

In choosing a solvent, various phase behavior characteristics of the solvent-solute mixtures are considered. For example, vapor-liquid equilibrium (VLE) behavior is important when accounting for the emission of solvent from reaction mixtures, and liquid-liquid miscibility (LLE) is important when a second solvent is used to extract target molecules from the reaction media. For solubility calculations, solid-liquid equilibrium (SLE) is a key property when product isolation is done through crystallization at reduced temperature or with the addition of anti-solvent.

For many applications, hundreds of typical solvents, not to mention an almost infinite number of mixtures thereof, are candidates in the solvent selection process. In most cases, there is simply insufficient phase equilibrium data on which to make an informed solvent selection. For example, in pharmaceutical applications, it is often the case that phase equilibrium data involving new drug molecules in the solvents simply do not exist. Although limited solubility experiments may be taken as part of the trial and error process, solvent selection is largely dictated by researchers' preferences or prior experiences.

Many solubility estimation techniques have been used to model the solubility of components in chemical mixtures. Some examples include the Hansen model and the UNIFAC group contribution model. Unfortunately, these models are rather inadequate because they have been developed mainly for petrochemicals with molecular weights in the 10 s and the low 100 s daltons. These models do not extrapolate well for chemicals with larger molecular weights, such as those encountered in pharmaceutical applications. Pharmaceuticals are mostly large, complex molecules with molecular weight in the range of about 200-600 daltons.

Perhaps, the most commonly used methods in solvent selection process are the solubility parameter models, i.e., the regular solution theory and the Hansen solubility parameter model. There are no binary parameters in these solubility parameter models and they all follow merely an empirical guide of "like dissolves like." The regular solution model is applicable to nonpolar solutions only, but not for solutions where polar or hydrogen-bonding interactions are significant. The Hansen model extends the solubility parameter concept in terms of three partial solubility parameters to better account for polar and hydrogen-bonding effects.

In his book, Hansen published the solubility parameters for over 800 solvents. See Hansen, C. M., HANSEN, SOLUBILITY PARAMETERS: A USER'S HANDBOOK (2000). Since Hansen's book contains the parameters for most common solvents, the issue in using the Hansen model lies in the determination of the Hansen solubility parameters from regression of available solubility data for the solute of interest in the solvent selection process. Once determined, these Hansen parameters provide a basis for calculating activity coefficients and solubilities for the solute in all the other solvents in the database. For pharmaceutical process design, Bakken, et al. reported that the Hansen model can only correlate solubility data with ±200% in accuracy, and it offers little predictive capability. See Bakken, et al., *Solubility Modeling in Pharmaceutical Process Design*, paper presented at AspenTech User Group Meeting, New Orleans, La., Oct. 5-8, 2003, and Paris, France, Oct. 19-22, 2003.

When there are no data available, the UNIFAC functional group contribution method is sometimes used for solvent selection. In comparison to the solubility parameter models, UNIFAC's strength comes with its molecular thermodynamic foundation. It describes liquid phase nonideality of a mixture with the concept of functional groups. All molecules in the mixture are characterized with a set of pre-defined UNIFAC functional groups. The liquid phase nonideality is the result of the physical interactions between these functional groups and activity coefficients of molecules are derived from those of functional groups, i.e., functional group additivity rule. These physical interactions have been pre-determined from available phase equilibrium data of systems containing these functional groups. UNIFAC gives adequate phase equilibrium (VLE, LLE and SLE) predictions for mixtures with small nonelectrolyte molecules as long as these molecules are composed of the pre-defined set of functional groups or similar groups.

UNIFAC fails for systems with large complex molecules for which either the functional group additivity rule becomes invalid or due to undefined UNIFAC functional groups. UNIFAC is also not applicable to ionic species, an important issue for pharmaceutical processes. Another drawback with UNIFAC is that, even when valuable data become available, UNIFAC cannot be used to correlate the data. For pharmaceutical process design, Bakken et al., reported that the UNIFAC model only predicts solubilities with a RMS (root mean square) error on ln x of 2, or about ±500% in accuracy, and it offers little practical value. Id.

A need exists for new, simple, and practical methods of accurately modeling one or more physical properties of a mixture.

SUMMARY OF THE INVENTION

The present invention provides a new system and method for modeling the physical properties or behavior of chemical mixtures (e.g., chemical solutions or suspensions). Briefly, the molecular structure of one or more species in a chemical mixture is assigned one or more different types of "conceptual segments." An equivalent number is determined for each conceptual segment. This conceptual segment approach of the present invention is referred to as the Non-Random Two-Liquid Segment Activity Coefficient ("NRTL-SAC") model.

In some embodiments, this invention features a method of modeling at least one physical property of a mixture of at least two chemical species. In one embodiment, the method comprises the computer implemented steps of determining at least one conceptual segment for each of the chemical species, using the determined conceptual segments to compute at least one physical property of the mixture; and providing an analysis of the computed physical property. The step of determining at least one conceptual segment includes defining an identity and an equivalent number of each conceptual segment. The provided analysis forms a model of at least one physical property of the mixture.

In further embodiments, this invention includes a method of modeling at least one physical property of a mixture that includes at least three chemical species. In one embodiment, the method comprises the computer implemented steps of determining at least one conceptual segment for a first chemical species; determining at least one conceptual segment for a second chemical species; determining at least one conceptual segment for a third chemical species; using the determined conceptual segments for the first chemical species, the determined conceptual segments for the second chemical species, and the determined conceptual segments for the third chemical species to compute at least one physical property of the mixture; and providing an analysis of the computed physical property. For each conceptual segment, the steps of determining the conceptual segments include defining an identity and an equivalent number of the respective conceptual segment. The analysis forms a model of at least one physical property of the mixture.

In another embodiment, this invention features methods of modeling solubility of a pharmaceutical component of a mixture that includes at least one pharmaceutical component and at least one solvent. In one embodiment, the method comprises the computer implemented steps of determining at least one conceptual segment for the pharmaceutical component, determining at least one conceptual segment for the solvent, using the determined conceptual segment for the pharmaceutical component and the determined conceptual segment for the solvent to compute solubility of the pharmaceutical component in the mixture, and providing an analysis of the computed solubility. The steps of determining the conceptual segments include defining an identity and an equivalent number of the respective conceptual segment. The analysis forms a solubility model of the pharmaceutical component in the mixture.

In further embodiments, this invention features computer program products. In one embodiment, the computer program product comprises a computer usable medium and a set of computer program instructions embodied on the computer useable medium for modeling at least one physical property of a mixture of at least two chemical species. The computer program instructions include the instructions to determine at least one conceptual segment for each of the chemical species, use the determined conceptual segments to compute at least one physical property of the chemical mixture; and provide an analysis of the computed physical property. The program instructions for determining conceptual segments include instructions for defining an identity and an equivalent number of each conceptual segment. The analysis forms a model of at least one physical property of the mixture.

In yet a further embodiment, this invention features a computer system for modeling at least one physical property of a mixture of at least two chemical species. In one embodiment, the computer system comprises a user input means for determining chemical data from a user, a digital processor coupled to receive input (determined chemical data) from the input means, and an output means coupled to the digital processor. The digital processor hosts and executes a modeling system in working memory. The modeling system (i) uses the chemical data to determine at least one conceptual segment for each of the chemical species; (ii) uses the determined conceptual segments to compute at least one physical property of the chemical mixture, and; (iii) provides an analysis of the computed physical property. The modeling system determines a conceptual segment, in part, by defining an identity and an equivalent number of each conceptual segment. The analysis forms a model of at least one physical property of the mixture. The output means provides to the user the formed model of the physical property of the chemical mixture.

In some embodiments, this invention features a pharmaceutical compound manufactured by a process that includes a modeling method. The modeling method models at least one physical property of a mixture of at least two chemical species and comprises the computer implemented steps of determining at least one conceptual segment for each of the chemical species, using the determined conceptual segments to compute at least one physical property of the mixture; and providing an analysis of the computed physical property. The step of determining at least one conceptual segment includes defining an identity and an equivalent number of each conceptual segment. The provided analysis forms a model of at least one physical property of the mixture.

This invention provides for the fast, practical modeling of physical properties or behaviors of chemical mixtures, even when there is little or no experimental data to which the behavior of the mixture can be correlated. The formed models offer improved accuracy over most or all prior modeling methods. For example, this invention offers a simple and practical tool for practitioners to estimate solubility of various components of a chemical mixture (e.g., a mixture including a pharmaceutical component), even when there is little or no phase equilibrium data available for the mixture.

This invention provides for modeling of mixtures having significant hydrophobic interactions, significant polar interactions, and/or significant hydrogen-bonding interactions. This invention eliminates the need to characterize mixture constituents with sets of pre-defined functional groups and provides for the modeling of mixtures comprising large, complex molecules for which a functional group additivity rule becomes invalid and/or for which there are a number of un-defined functional groups.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 1:
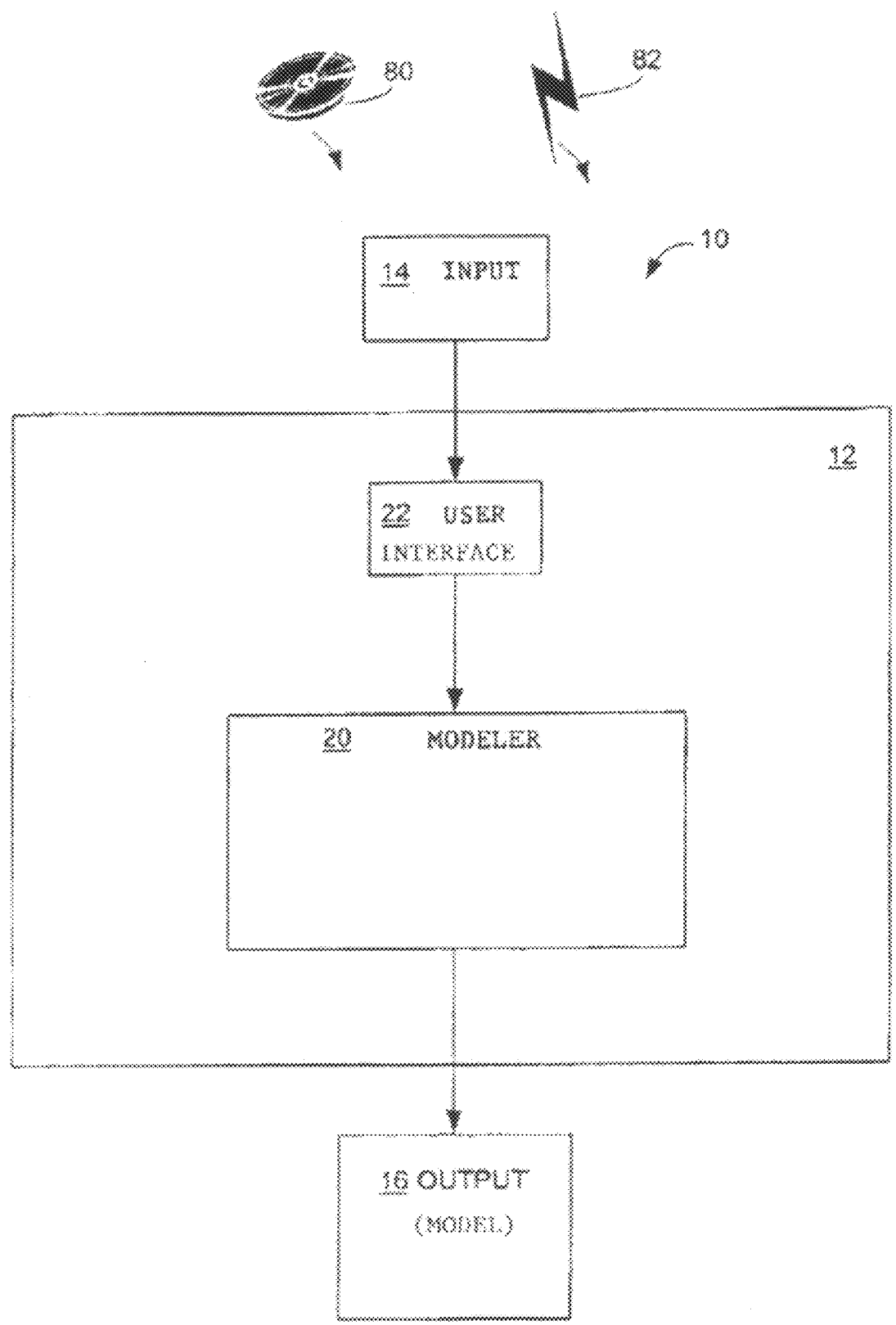
FIG. 1 is a block diagram of a computer system embodying the present invention modeling methods.

A description of preferred embodiments of the invention follows.

The NRTL-SAC model of the present invention follows the segment contribution concept that was first incorporated into the NRTL model as a Gibbs energy expression for oligomers and polymers. While the UNIFAC model of the prior art decomposes molecules into a large number of pre-defined functional groups, the NRTL-SAC model of the present invention decomposes or assigns to each molecular species a few pre-defined conceptual segments. For example, in some embodiments of the present invention, each molecular species is assigned three types of conceptual segments: a hydrophobic segment, a polar segment, and a hydrophilic segment. Each conceptual segment is then assigned an equivalent number. The equivalent numbers of these conceptual segments are determined, not from their exact molecular structure (as are the functional groups of the UNIFAC model), but from experimental data that reflect on their true molecular characteristics in the mixture. These equivalent numbers are used to describe or model how the various molecular species of a mixture interact with one another. In this manner, the NRTL-SAC methods of the present invention is able to model one or more physical properties of a mixture.

Various NRTL models have been used to model various types of mixtures. Previous segment-based NRTL models used "segments" to define the various chemical species of a mixture. Like the UNIFAC model, these segments were based upon the actual molecular structure of the various chemical species, while the conceptual segments of the present invention are defined based upon actual thermodynamic behavior of the various chemical species.

The segment contribution approach represents a practical alternative to the UNIFAC functional group contribution approach. Industrial practitioners generally have a healthy distrust or suspicion of "predictive" models, empirical or ab initio. Wherever possible, they prefer correlative models that allow them to validate the model with available data, determine the model parameters from the data, and extrapolate into new conditions with proper molecular insights and thermodynamic consistency. The NRTL-SAC model of the present invention offers such a framework, with molecular descriptors identified by using available experimental data for the chemical species of a mixture. The NRTL-SAC model is used to extrapolate to other chemical systems that are also described in terms of the same or similar set of molecular descriptors.

In some embodiments, this invention includes methods of modeling at least one physical property of a mixture of at least two chemical species. In one embodiment, the method comprises the computer implemented steps of (i) determining at least one conceptual segment for each of the chemical species; (ii) using the determined conceptual segments, computing at least one physical property of the mixture; and (iii) providing an analysis of the computed physical property. The step of determining a conceptual segment includes defining an identity and an equivalent number of each conceptual segment. The analysis forms a model of at least one physical property of the mixture.

The methods of this invention can model mixtures that include one or more liquid phases. In some embodiments, at least a portion of at least one chemical species of the mixture is in at least one fluid phase (e.g., a vapor phase and/or a liquid phase). For example, the mixture can include one or more liquid phases (e.g., two or more liquid solvent phases) and a vapor phase. In further embodiments, at least a portion of at least one chemical species of the mixture is in one or more solid phases. In yet further embodiments, the mixture includes at least one solid phase and at least one liquid phase. In still further embodiments, the mixture includes at least one solid phase (e.g., at least 1, 2, 3, or more than 3 solid phases), at least one liquid phase (e.g., at least 1, 2, 3, or more than 3 liquid phases), and a vapor phase.

The methods of this invention can model a wide range of chemical mixtures. For example, the chemical mixtures can include one or more of the following types of chemical species: an organic nonelectrolyte, an organic salt, a compound possessing a net charge, a zwitterions, a polar compound, a nonpolar compound, a hydrophilic compound, a hydrophobic compound, a petrochemical, a hydrocarbon, a halogenated hydrocarbon, an ether, a ketone, an ester, an amide, an alcohol, a glycol, an amine, an acid, water, an alkane, a surfactant, a polymer, and an oligomer.

In further embodiments, the mixture includes at least one chemical species which is a solvent (e.g., a solvent used in a pharmaceutical production, screening, or testing process), a solute, a pharmaceutical component, a compound used in an agricultural application (e.g., a herbicide, a pesticide, or a fertilizer) or a precursor of a compound used in an agricultural application, a compound used in an adhesive composition or a precursor of a compound used in an adhesive composition, a compound used in an ink composition or a precursor of a compound used in an ink composition. As used herein, a "pharmaceutical component" includes a pharmaceutical compound, drug, therapeutic agent, or a precursor thereof (i.e., a compound used as an ingredient in a pharmaceutical compound production process). In some embodiments, the mixture includes at least one pharmaceutical component having a molecular weight greater than about 900 daltons, at least one pharmaceutical component having a molecular weight in the range of between about 100 daltons and about 900 daltons, and/or at least one pharmaceutical component having a molecular weight in the range of between about 200 daltons and about 600 daltons. In further embodiments, the mixture includes at least one nonpolymeric pharmaceutical component.

In further embodiments, the mixture includes at least one ICH solvent, which is a solvent listed in the *ICH Harmonized Tripartite Guideline, Impurities: Guideline for Residual Solvents Q3C*, incorporated herein in its entirety by reference. ICH STEERING COMMITTEE, *ICH Harmonized Tripartite Guideline, Impurities: Guideline for Residual Solvents Q3C*, International Conference of Harmonization of Technical Requirements for Registration of Pharmaceuticals for Human Use (1997).

It will be apparent to those skilled in the art that a component of the mixture can belong to more than one type of chemical species.

In accordance with one aspect of the present invention, at least one conceptual segment (e.g., at least 1, 2, 3, 4, 5, 7, 10, 12, or more than 12 conceptual segments) is determined or defined for each of the chemical species of the mixture. The conceptual segments are molecular descriptors of the various molecular species in the mixture. An identity and an equivalent number are determined for each of the conceptual segments. Examples of identities for conceptual segments include a hydrophobic segment, a polar segment, a hydrophilic segment, a charged segment, and the like. Experimental phase equilibrium data can be used to determine the equivalent number of the conceptual segment(s).

The determined conceptual segments are used to compute at least one physical property of the mixture, and an analysis of the computed physical property is provided to form a model of at least one physical property of the mixture. The methods of this invention are able to model a wide variety of physical properties. Examples of physical properties include vapor pressure, solubility (e.g., the equilibrium concentration of one or more chemical species in one or more phases of the mixture), boiling point, freezing point, octanol/water partition coefficient, lipophilicity, and other physical properties that are measured or determined for use in the chemical processes.

In some embodiments, the mixture includes at least two liquid phases and the modeled physical property or properties include the solubility of one or more chemical species in the two liquid phases. In other embodiments, the mixture includes at least one liquid phase and at least one solid phase, and the modeled physical property or properties include the solubility of a chemical species of the solid phase in the liquid phase.

Preferably, the methods provide equilibrium values of the physical properties modeled. For example, a mixture can include at least one liquid solvent and at least one solid pharmaceutical component and the methods can be used to model the solubility of the pharmaceutical component. In this way, the method can provide the amount (e.g., a concentration value) of the pharmaceutical component that will be dissolved in the solvent at equilibrium. In another example, the method could model a mixture that includes a solid phase (e.g., a solid pharmaceutical component) and at least two liquid phases (e.g., two solvent that are immiscible in one another). The model can predict, or be used to predict, how much of the pharmaceutical component will be dissolved in the two liquid phases and how much will be left in the solid phase at equilibrium. In yet a further embodiment, the methods can be used to predict the behavior of a mixture after a change has occurred. For example, if the mixture includes two liquid phases and one solid phase, and an additional chemical species is introduced into the mixture (e.g., a solvent, pharmaceutical component, or other chemical compound), additional amounts of a chemical species are introduced into the mixture, and/or one or more environmental conditions are changed (e.g., a change in temperature and/or pressure), the method can be used to predict how the introduction of the chemical species and/or change in conditions will alter one or more physical properties of the mixture at equilibrium.

The models of the physical property or properties of the mixture are produced by determining the interaction characteristics of the conceptual segments. In some embodiments, the segment-segment interaction characteristics of the conceptual segments are represented by their corresponding binary NRTL parameters. Given the NRTL parameters for the conceptual segments and the molecular descriptors for the molecules, the NRTL-SAC model computes activity coefficients for the segments and then for the various molecules in the mixture. In other words, the physical properties or behavior of the mixture will be accounted for based on the segment compositions of the molecules and their mutual interactions. The activity coefficient of each molecule is computed from the number and type of segments for each molecule and the corresponding segment activity coefficients.

In further embodiments, this invention includes a method of modeling at least one physical property of a mixture that includes at least three chemical species. In one embodiment, the method comprises the computer implemented steps of (i) determining at least one conceptual segment for a first chemical species; (ii) determining at least one conceptual segment for a second chemical species; (iii) determining at least one conceptual segment for a third chemical species; (iv) using the determined conceptual segments for the first chemical species, the determined conceptual segments for the second chemical species and the determined conceptual segments for the third chemical species (e.g., a pharmaceutical component), computing at least one physical property of the mixture; and (v) providing an analysis of the computed physical property. Each step of determining the conceptual segments includes defining an identity and an equivalent number of the respective conceptual segment. The analysis forms a model of at least one physical property of the mixture.

In further embodiments, this invention features methods of modeling solubility of a pharmaceutical component of a mixture that includes at least one pharmaceutical component and at least one solvent. The methods comprise the computer implemented steps of (i) determining at least one conceptual segment for the pharmaceutical component; (ii) determining at least one conceptual segment for the solvent; (iii) using the determined conceptual segment for the pharmaceutical component and the determined conceptual segment for the solvent, computing solubility of the pharmaceutical component in the mixture; and (iv) providing an analysis of the computed solubility. The analysis forms a solubility model of the pharmaceutical component in the mixture.

In some embodiments, this invention features computer program products. The computer program products comprise a computer usable medium and a set of computer program instructions embodied on the computer useable medium for modeling at least one physical property of a mixture of at least two chemical species. Included are (a) instructions to determine at least one conceptual segment for each of the chemical species; (b) instructions to use the determined conceptual segments to compute at least one physical property of the chemical mixture; and (c) instructions to provide an analysis of the computed physical property, wherein the analysis forms a model of at least one physical property of the mixture.

Referring now to FIG. 1, illustrated is a computer system 10 embodying the present invention modeling methods mentioned above. Generally, computer system 10 includes digital processor 12 which hosts and executes modeler 20. Modeler 20 comprises the modeling method of the invention in working memory. Input means 14 provides user selectable/definable chemical data (e.g., data relating to, or useful for, modeling a mixture that includes a pharmaceutical component) from a user of computer system 10. Input means 14 can be implemented as any of various in-put/out-put devices, programs, or routines coupled to computer system 10.

Responsive to input means 14 is user interface 22. User interface 22 receives user input data from input means 14 and provides input data for processing by modeler 20. Modeler 20 determines at least one physical property of a mixture that includes at least one user input compound. Modeler 20 further provides an analysis of the determined physical properties and thus outputs a model 16 of the determined physical property. As such, output 16 is a model of at least one physical property of a mixture (e.g., a mixture including one or more pharmaceutical components) derived based on the chemical data from input 14.

In one embodiment, computer program product 80, including a computer readable medium (e.g., a removable storage medium such as one or more DVD-ROM's, CD-ROM's, diskettes, tapes, etc.) provides at least a portion of the software instructions for modeler 20, user interface 22, and/or any of component of modeler 20 or user interface 22. Computer program product 80 can be installed by any suitable software installation procedure, as is well known in the art. In another embodiment, at least a portion of the software instructions may also be downloaded over a wireless connection. Computer program propagated signal product 82 embodied on a propagated signal on a propagation medium (e.g., a radio wave, an infrared wave, a laser wave, a sound wave, or an electrical wave propagated over a global network such as the Internet, or other network(s)) provides at least a portion of the software instructions for modeler 20, user interface 22, and/or any component of modeler 20 or user interface 22.

In alternate embodiments, the propagated signal is an analog carrier wave or digital signal carried on the propagated medium. For example, the propagated signal may be a digitized signal propagated over a global network (e.g., the Internet), a telecommunications network, or other network. In one embodiment, the propagated signal is a signal that is transmitted over the propagation medium over a period of time, such as the instructions for a software application sent in packets over a network over a period of milliseconds, seconds, minutes, or longer. In another embodiment, the computer readable medium of computer program product 80 is a propagation medium that the computer system 10 may receive and read, such as by receiving the propagation medium and identifying a propagated signal embodied in the propagation medium, as described above for computer program propagated signal product 82.

Figure 2:
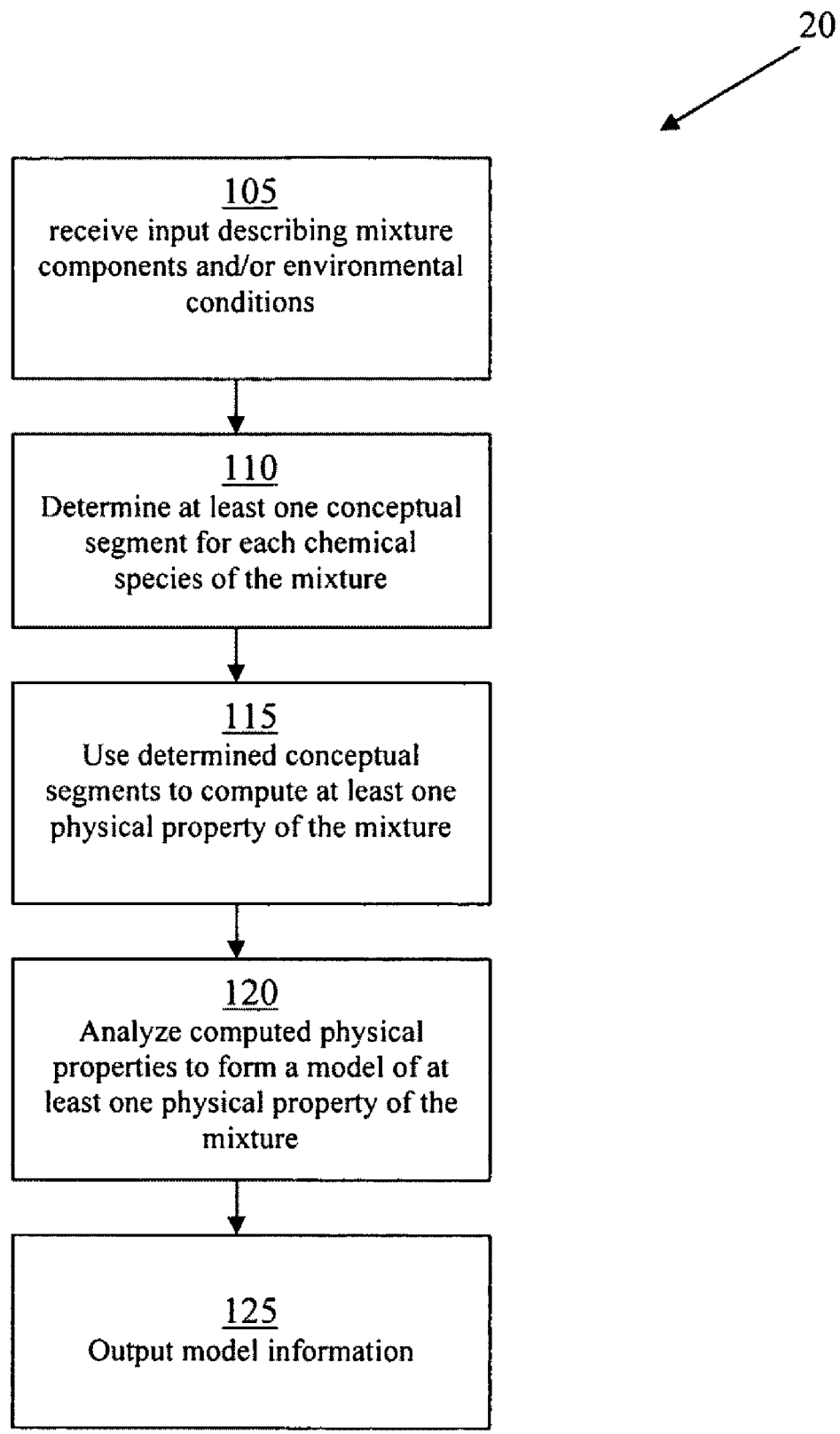
FIG. 2 illustrates data flow and process steps for a modeler of the present invention, such as that employed in the embodiment of FIG. 1.
Figure 3:
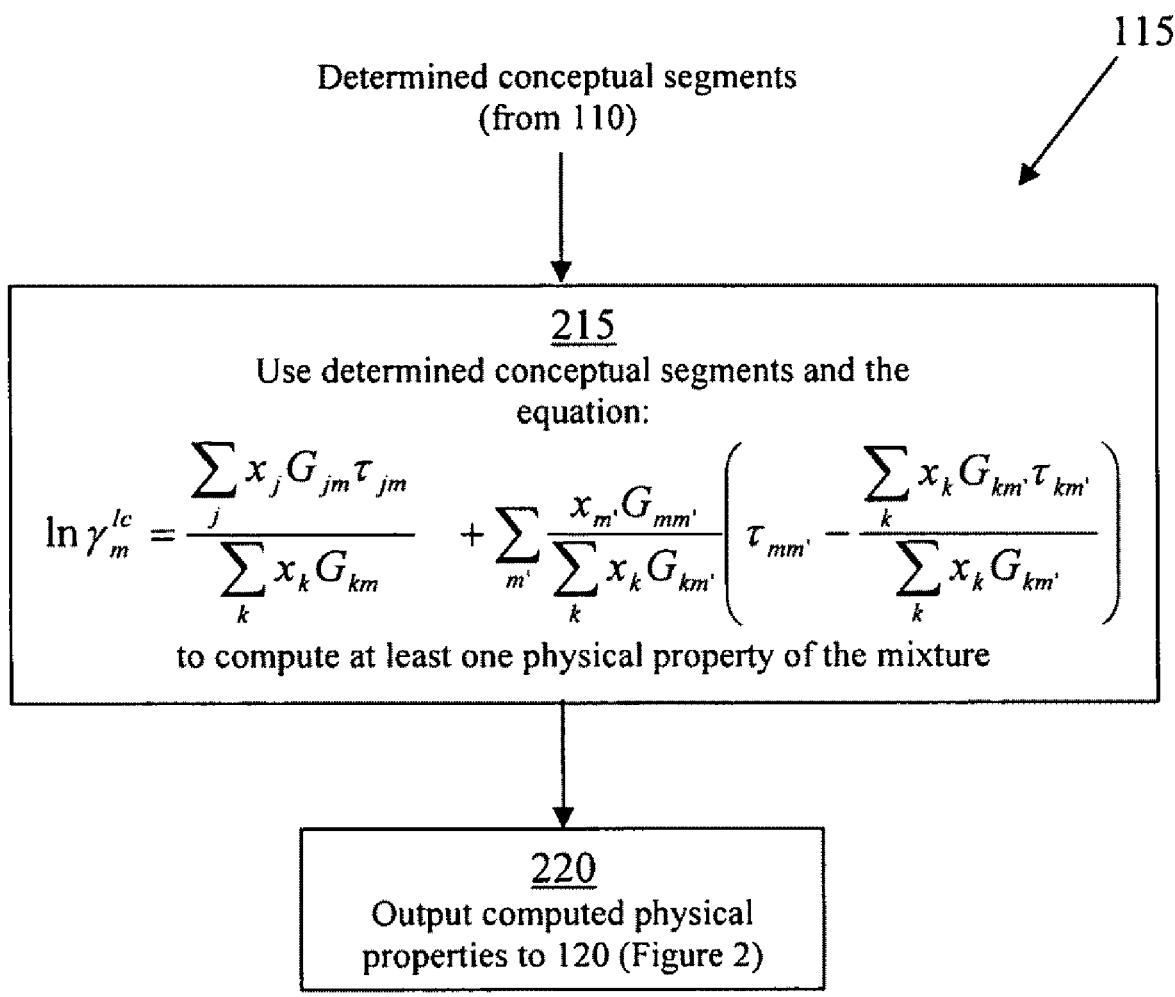
FIG. 3 illustrates data flow and process steps for a computation by the modeler of FIG. 2.

FIGS. 2 and 3 illustrate data flow and process steps for a modeler performing the methods of the invention, such as modeler 20 of FIG. 1. With reference to FIG. 2, chemical data describing one or more chemical species of the mixture and/or environmental conditions (e.g., pressure and/or temperature) is entered at step 105 of the modeler process. Step 110 uses that data to determine at least one conceptual segment for each chemical species of the mixture. The determined conceptual segments are used to compute at least one physical property of the mixture during step 115. The computed physical properties are analyzed to form a model of at least one physical property of the mixture (e.g., solubility of one or more chemical species in one or more phases of the mixture) in step 120. The model information is then given as output at step 125. The output can take the form of data or an analysis appearing on a computer monitor, data or instructions sent to a process control system or device, data entered into a data storage device, and/or data or instructions relayed to additional computer systems or programs.

FIG. 3 illustrates in more detail the computation at step 115 in FIG. 2. Step 115 begins with the receipt of determined conceptual segments for each chemical species of the mixture. The determined conceptual segments and the equation:

$$\ln \gamma_m^{lc} = \frac{\sum_j x_j G_{jm} \tau_{jm}}{\sum_k x_k G_{km}} + \sum_{m'} \frac{x_{m'} G_{mm'}}{\sum_k x_k G_{km'}} \left( \tau_{mm'} - \frac{\sum_k x_k G_{km'} \tau_{km'}}{\sum_k x_k G_{km'}} \right)$$

are used to compute at least one physical property of the mixture during step 215. The computed physical properties are provided as output 220 from computation step 215. In step 220, the computed physical properties are passed to step 120 of FIG. 2 for forming a model of the physical property of the mixture as described above.

According to the foregoing, in some embodiments, the invention features a computer system for modeling at least one physical property of a mixture of at least two chemical species. The computer system is formed of a user input means for determining chemical data from a user, a digital processor coupled to receive input from the input means, and an output means coupled to the digital processor. The digital processor hosts and executes a modeling system in working memory. The modeling system (i) uses the chemical data to determine at least one conceptual segment for each of the chemical species; (ii) uses the determined conceptual segments to compute at least one physical property of the chemical mixture; and (iii) provides an analysis of the computed physical property. The analysis forms a model of the at least one physical property of the mixture. The output means provides to the user of the formed model of the physical property of the chemical mixture.

In some embodiments, this invention features a pharmaceutical compound manufactured by a process that includes a modeling method. The modeling method models at least one physical property of a mixture of at least two chemical species and comprises the computer implemented steps of determining at least one conceptual segment for each of the chemical species, using the determined conceptual segments to compute at least one physical property of the mixture; and providing an analysis of the computed physical property. The step of determining at least one conceptual segment includes defining an identity and an equivalent number of each conceptual segment. The provided analysis forms a model of at least one physical property of the mixture.

The following Examples are illustrative of the invention, and are not meant to be limiting in any way.

Example 1

Modeling a Mixture of Nonelectrolyte Chemical Species

A study was performed to determine how well the NRTL-SAC models the solubility of mixtures comprising a solid organic nonelectrolyte.

The solubility of a solid organic nonelectrolyte is described well by the expression:

$$\ln x_I^{SAT} = \frac{\Delta_{fus} S}{R}\left(1 - \frac{T_m}{T}\right) - \ln \gamma_I^{SAT}$$

for $T \leq T_m$ and where the entropy of fusion of the solid ($\Delta_{fus} S$) is represented by:

$$\Delta_{fus} S = \frac{\Delta_{fus} H}{T_m}$$

$x_I^{SAT}$ is the mole fraction of the solid (the solute) dissolved in the solvent phase at saturation, $\gamma_I^{SAT}$ is the activity coefficient for the solute in the solution at saturation, R is the gas constant, T is the temperature, and $T_m$ is the melting point of the solid. Given a polymorph, $\Delta_{fus} S$ and $T_m$ are fixed and the solubility is then a function of temperature and activity coefficient of the solute in the solution. The activity coefficient of the solute in the solution plays the key role in determining the solubility. In general, the activity coefficient of the solute in the solution is usually calculated from a liquid activity coefficient model.

Except for the ideal solution model, an activity coefficient model is often written in two parts as such:

$$\ln \gamma_I = \ln \gamma_I^C + \ln \gamma_I^R$$

$\gamma_I^C$ and $\gamma_I^R$ are the combinatorial and residual contributions to the activity coefficient of component I, respectively.

In NRTL-SAC, the combinatorial part, $\gamma_I^C$, is calculated from the Flory-Huggins term for the entropy of mixing. The residual part, $\gamma_I^R$, is set equal to the local composition (lc) interaction contribution, $\gamma_I^{lc}$:

$$\ln \gamma_I^R = \ln \gamma_I^{lc} = \sum_m r_{m,I} \lfloor \ln \gamma_m^{lc} - \ln \gamma_m^{lc,I} \rfloor$$

with $$\ln \gamma_m^{lc} = \frac{\sum_j x_j G_{jm} \tau_{jm}}{\sum_k x_k G_{km}} + \sum_{m'} \frac{x_{m'} G_{mm'}}{\sum_k x_k G_{km'}}\left(\tau_{mm'} - \frac{\sum_k x_k G_{km'} \tau_{km'}}{\sum_k x_k G_{km'}}\right),$$

$$\ln \gamma_m^{lc,I} = \frac{\sum_j x_{j,I} G_{jm} \tau_{jm}}{\sum_k x_{k,I} G_{km}} + \sum_{m'} \frac{x_{m',I} G_{mm'}}{\sum_k x_{k,I} G_{km'}}\left(\tau_{mm'} - \frac{\sum_k x_{k,I} G_{km'} \tau_{km'}}{\sum_k x_{k,I} G_{km'}}\right),$$

$$x_j = \frac{\sum_J x_J r_{j,J}}{\sum_I \sum_i x_I r_{i,I}},$$

$$x_{j,I} = \frac{r_{j,I}}{\sum_j r_{j,I}},$$

where i, j, k, m, m' are the segment-based species index, I, J are the component index, $x_j$ is the segment-based mole fraction of segment species j, and $x_J$ is the mole fraction of component J, $r_{m,I}$ is the number of segment species m contained in component I, $\gamma_m^{lc}$ is the activity coefficient of segment species m, and $\gamma_m^{lc,I}$ is the activity coefficient of segment species m contained only in component I. G and τ are local binary quantities related to each other by the NRTL non-random factor parameter α:

$$G = \exp(-\alpha \tau)$$

The equation:

$$\ln \gamma_I^R = \ln \gamma_I^{lc} = \sum_m r_{m,I} \lfloor \ln \gamma_m^{lc} - \ln \gamma_m^{lc,I} \rfloor$$

is a general form for the local composition interaction contribution to activity coefficients of components in the NRTL-SAC model of the present invention. For mono-segment solvent components (S), this equation can be simplified and reduced to the classical NRTL model as follows:

$$\ln \gamma_{I=S}^{lc} = \sum_m r_{m,S} \lfloor \ln \gamma_m^{lc} - \ln \gamma_m^{lc,S} \rfloor$$

with $r_{m,S} = 1$, $\ln \gamma_m^{lc,S} = 0$.

Therefore, $$\ln \gamma_{I=S}^{lc} = \frac{\sum_j x_j G_{jS} \tau_{jS}}{\sum_k x_k G_{kS}} + \sum_m \frac{x_m G_{Sm}}{\sum_k x_k G_{km}}\left(\tau_{Sm} - \frac{\sum_k x_k G_{km} \tau_{km}}{\sum_k x_k G_{km}}\right),$$

where $G_{jS} = \exp(-\alpha_{jS} \tau_{jS})$, $G_{Sj} = \exp(-\alpha_{jS} \tau_{Sj})$.

This is the same equation as the classical NRTL model.

Three conceptual segments were defined for nonelectrolyte molecules: a hydrophobic segment, a polar segment, and a hydrophilic segment. These conceptual segments qualitatively capture the phase behavior of real molecules and their corresponding segments. Real molecules in turn are used as reference molecules for the conceptual segments and available phase equilibrium data of these reference molecules are used to identify NRTL binary parameters for the conceptual segments. Preferably, these reference molecules possess distinct molecular characteristics (i.e., hydrophobic, hydrophilic, or polar) and have abundant, publicly available, thermodynamic data (e.g., phase equilibrium data).

The study was focused on the 59 ICH solvents used in pharmaceutical process design. Water, triethylamine, and n-octanol were also considered. Table 1 shows these 62 solvents and the solvent characteristics.

TABLE 1

Common Solvents in Pharmaceutical Process Design

| Solvent (Component 1) | $\tau_{12}{}^a$ | $\tau_{21}{}^a$ | $\tau_{12}{}^b$ | $\tau_{21}{}^b$ | $\tau_{12}{}^c$ | $\tau_{21}{}^c$ | Solvent characteristics |
|---|---|---|---|---|---|---|---|
| ACETIC-ACID | 1.365 | 0.797 | 2.445 | −1.108 | | | Complex |
| ACETONE | 0.880 | 0.935 | 0.806 | 1.244 | | | Polar |
| ACETONITRILE | 1.834 | 1.643 | 0.707 | 1.787 | | | Polar |
| ANISOLE | | | | | | | Hydrophobic |
| BENZENE | 1.490 | −0.614 | | | 3.692 | 5.977 | Hydrophobic |
| 1-BUTANOL | −0.113 | 2.639 | 0.269 | 2.870 | −2.157 | 5.843 | Hydrophobic/Hydrophilic |
| 2-BUTANOL | −0.165 | 2.149 | −0.168 | 3.021 | −1.539 | 5.083 | Hydrophobic/Hydrophilic |
| N-BUTYL-ACETATE | | | 1.430 | 2.131 | | | Hydrophobic/Polar |
| METHYL-TERT-BUTYL-ETHER | −0.148 | 0.368 | 1.534 | 4.263 | | | Hydrophobic |
| CARBON-TETRACHLORIDE | 1.309 | −0.850 | | | 5.314 | 7.369 | Hydrophobic |
| CHLOROBENZENE | 0.884 | −0.194 | | | 4.013 | 7.026 | Hydrophobic |
| CHLOROFORM | 1.121 | −0.424 | | | 3.587 | 4.954 | Hydrophobic |
| CUMENE | | | | | | | Hydrophobic |
| CYCLOHEXANE | −0.824 | 1.054 | | | 6.012 | 9.519 | Hydrophobic |
| 1,2-DICHLOROETHANE | 1.576 | −0.138 | 3.207 | 4.284 | 2.833 | 4.783 | Hydrophobic |
| 1,1-DICHLOROETHYLENE | | | | | | | Hydrophobic |
| 1,2-DICHLOROETHYLENE | | | | | | | Hydrophobic |
| DICHLOROMETHANE | 0.589 | 0.325 | 1.983 | 3.828 | | | Polar |
| 1,2-DIMETHOXYETHANE | | | 0.450 | 1.952 | | | Polar |
| N,N-DIMETHYLACETAMIDE | | | −0.564 | 1.109 | | | Polar |
| N,N-DIMETHYLFORMAMIDE | 1.245 | 1.636 | −1.167 | 2.044 | | | Polar |
| DIMETHYL-SULFOXIDE | | | −2.139 | 0.955 | | | Polar |
| 1,4-DIOXANE | 1.246 | 0.097 | 1.003 | 1.010 | | | Polar |
| ETHANOL | 0.533 | 2.192 | −0.024 | 1.597 | | | Hydrophobic/Hydrophilic |
| 2-ETHOXYETHANOL | −0.319 | 2.560 | −1.593 | 1.853 | | | Hydrophobic/Hydrophilic |
| ETHYL-ACETATE | 0.771 | 0.190 | | | 0.508 | 3.828 | Hydrophobic/Polar |
| ETHYLENE-GLYCOL | | | 1.380 | −1.660 | | | Hydrophilic |
| DIETHYL-ETHER | −0.940 | 1.400 | | | 1.612 | 3.103 | Hydrophobic |
| ETHYL-FORMATE | | | | | | | Polar |
| FORMAMIDE | | | | | | | Complex |
| FORMIC-ACID | | | −0.340 | −1.202 | | | Complex |
| N-HEPTANE | −0.414 | 0.398 | | | | | Hydrophobic |
| N-HEXANE | | | 6.547 | 10.949 | 6.547 | 10.949 | Hydrophobic |
| ISOBUTYL-ACETATE | | | | | | | Polar |
| ISOPROPYL-ACETATE | | | | | | | Polar |
| METHANOL | 1.478 | 1.155 | 0.103 | 0.396 | | | Hydrophobic/Hydrophilic |
| 2-METHOXYETHANOL | | | 1.389 | −0.566 | | | Hydrophobic/Hydrophilic |
| METHYL-ACETATE | | | 0.715 | 2.751 | | | Polar |
| 3-METHYL-1-BUTANOL | 0.062 | 2.374 | −0.042 | 3.029 | −0.598 | 5.680 | Hydrophobic/Hydrophilic |
| METHYL-BUTYL-KETONE | | | | | | | Hydrophobic/Polar |
| METHYLCYCLOHEXANE | 1.412 | −1.054 | | | | | Polar |
| METHYL-ETHYL-KETONE | −0.036 | 1.273 | 0.823 | 2.128 | −0.769 | 3.883 | Hydrophobic/Polar |
| METHYL-ISOBUTYL-KETONE | | | 0.977 | 4.868 | | | Hydrophobic/Polar |
| ISOBUTANOL | 0.021 | 2.027 | 0.592 | 2.702 | −1.479 | 5.269 | Hydrophobic/Hydrophilic |
| N-METHYL-2-PYRROLIDONE | −0.583 | 3.270 | −0.235 | 0.437 | | | Hydrophobic |
| NITROMETHANE | | | 1.968 | 2.556 | | | Polar |
| N-PENTANE | 0.496 | −0.523 | | | | | Hydrophobic |
| 1-PENTANOL | −0.320 | 2.567 | −0.029 | 3.583 | | | Hydrophobic/Hydrophilic |
| 1-PROPANOL | 0.049 | 2.558 | 0.197 | 2.541 | | | Hydrophobic/Hydrophilic |
| ISOPROPYL-ALCOHOL | 0.657 | 1.099 | 0.079 | 2.032 | | | Hydrophobic/Hydrophilic |
| N-PROPYL-ACETATE | | | 1.409 | 2.571 | | | Hydrophobic/Polar |
| PYRIDINE | −0.665 | 1.664 | −0.990 | 3.146 | | | Polar |
| SULFOLANE | | | 1.045 | 0.396 | | | Polar |
| TETRAHYDROFURAN | 0.631 | 1.981 | 1.773 | 0.563 | | | Polar |
| 1,2,3,4-TETRAHYDRONAPHTHALENE | 1.134 | −0.631 | | | | | Hydrophobic |
| TOLUENE | −0.869 | 1.292 | | | 4.241 | 7.224 | Hydrophobic |
| 1,1,1-TRICHLOROETHANE | 0.535 | −0.197 | | | | | Hydrophobic |
| TRICHLOROETHYLENE | 1.026 | −0.560 | | | | | Hydrophobic |
| M-XYLENE | | | | | | | Hydrophobic |
| WATER | 10.949 | 6.547 | | | | | Hydrophilic |

TABLE 1-continued

Common Solvents in Pharmaceutical Process Design

| Solvent (Component 1) | $\tau_{12}{}^a$ | $\tau_{21}{}^a$ | $\tau_{12}{}^b$ | $\tau_{21}{}^b$ | $\tau_{12}{}^c$ | $\tau_{21}{}^c$ | Solvent characteristics |
|---|---|---|---|---|---|---|---|
| TRIETHYLAMINE | −0.908 | 1.285 | 1.200 | 1.763 | −0.169 | 4.997 | Hydrophobic/Polar |
| 1-OCTANOL | −0.888 | 3.153 | | | 0.301 | 8.939 | Hydrophobic/Hydrophilic |

Wherein:
1. $\tau_{12}{}^a$ and $\tau_{21}{}^a$ are NRTL binary τ parameters for systems of the listed solvents and hexane. NRTL non-random factor parameter, α, is fixed as a constant of 0.2. In these binary systems, solvent is component 1 and hexane component 2. τ's were determined from available VLE & LLE data.
2. $\tau_{12}{}^b$ and $\tau_{21}{}^b$ are NRTL binary τ parameters for systems of the listed solvents and water. NRTL non-random factor parameter, α, is fixed as a constant of 0.3. In these binary systems, solvent is component 1 and water component 2. τ's were determined from available VLE data.
3. $\tau_{12}{}^c$ and $\tau_{21}{}^c$ are NRTL binary τ parameters for systems of the listed solvents and water. NRTL non-random factor parameter, α, is fixed as a constant of 0.2. In these binary systems, solvent is component 1 and water component 2. τ's were determined from available LLE data.

Hydrocarbon solvents (aliphatic or aromatic), halogenated hydrocarbons, and ethers are mainly hydrophobic. Ketones, esters and amides are both hydrophobic and polar. Alcohols, glycols, and amines may have both substantial hydrophilicity and hydrophobicity. Acids are complex, with hydrophilicity, polarity, and hydrophobicity.

Also shown in Table 1 are the available NRTL binary parameters (τ) for various solvent-water binary systems and solvent-hexane binary systems. Applicants obtained these binary parameters from fitting selected literature phase equilibrium data and deliberately ignoring the temperature dependency of these parameters. These values illustrate the range of values for these binary parameters. Note that many of the binary parameters are missing, as the phase equilibrium data is not found in the literature or simply has never been determined for that solvent mixture. Also note the sheer number of binary parameters needed for the prior art NRTL models for even a moderately sized system of solvents. For example, to model 60 solvents with the NRTL model, 60×60 NRTL binary parameters would be needed.

Table 1 shows that, for the NRTL binary parameters determined from VLE and LLE data for hydrophobic solvent (1)/water (2) binaries, all hydrophobic solvents exhibit similar repulsive interactions with water and both $\tau_{12}$ and $\tau_{21}$ are large positive values for the solvent-water binaries. When the hydrophobic solvents also carry significant hydrophilic or polar characteristics, $\tau_{12}$ becomes negative while $\tau_{21}$ retain a large positive value.

Table 1 also illustrates that similar repulsive, but weaker, interactions between a polar solvent (1) and hexane (2), a representative hydrophobic solvent. Both $\tau_{12}$ and $\tau_{21}$ are small, positive values for the solvent-hexane binaries. The interactions between hydrophobic solvents and hexane are weak and the corresponding NRTL binary parameters are around or less than unity, characteristic of nearly ideal solutions.

The interactions between polar solvents (1) and water (2) are more subtle. While all $\tau_{21}$ are positive, $\tau_{12}$ can be positive or negative. This is probably due to different polar molecules exhibiting different interactions, some repulsive and others attractive, with hydrophilic molecules.

Hexane and water were chosen as the reference molecule for hydrophobic segment and for hydrophilic segment, respectively. The selection of reference molecule for polar segment requires attention to the wide variations of interactions between polar molecules and water. Acetonitrile was chosen as the reference molecule for a polar segment, and a mechanism was introduced to tune the way the polar segment is characterized. The tuning mechanism, as shown in Table 2, allows tuning of the interaction characteristics between the polar segment and the hydrophilic segment. In other words, instead of using only one polar segment ("Y"), two polar segments ("Y−" and "Y+") were used. The difference between Y− and Y+ is the way they interact with the hydrophilic segment.

The chosen values for the NRTL binary interactions parameters, α and τ, for the three conceptual segments are summarized in Table 2.

TABLE 2

NRTL Binary Parameters for Conceptual Segments in NRTL-SAC

| | Segment (1) | | | | |
|---|---|---|---|---|---|
| | X (hydrophobic segment) | X (hydrophobic segment) | Y− (polar segment) | Y+ (polar segment) | X (hydrophobic segment) |
| | Segment (2) | | | | |
| | Y− (polar segment) | Z (hydrophilic segment) | Z (hydrophilic segment) | Z (hydrophilic segment) | Y+ (polar segment) |
| $\tau_{12}$ | 1.643 | 6.547 | −2.000 | 2.000 | 1.643 |
| $\tau_{21}$ | 1.834 | 10.949 | 1.787 | 1.787 | 1.834 |
| $\alpha_{12} = \alpha_{21}$ | 0.2 | 0.2 | 0.3 | 0.3 | 0.2 |

As a first approximation, the temperature dependency of the binary parameters was ignored.

The binary parameters for the hydrophobic segment (1)—hydrophilic segment (2) were determined from available liquid-liquid equilibrium data of hexane-water binary mixture (see Table 1). α was fixed at 0.2 because it is the customary value for α for systems that exhibit liquid-liquid separation. Here both $\tau_{12}$ and $\tau_{21}$ are large positive values (6.547, 10.950). They highlight the strong repulsive nature of the interactions between the hydrophobic segment and the hydrophilic segment.

Determining a suitable value for α is known in the art. See J. M. PRAUSNITZ, ET AL., MOLECULAR THERMODYNAMICS OF FLUID-PHASE EQUILIBRIA 261 (3d ed. 1999).

The binary parameters for the hydrophobic segment (1)—polar segment (2) were determined from available liquid-liquid equilibrium data of hexane—acetonitrile binary mixture (see Table 1). Again, α was fixed at 0.2. Both $\tau_{12}$ and $\tau_{21}$ were small positive values (1.643, 1.834). They highlight the weak repulsive nature of the interactions between hydrophobic segment and polar segment.

The binary parameters for the hydrophilic segment (1)—polar segment (2) were determined from available vapor-liquid equilibrium data of water—acetonitrile binary mixture (see Table 1). α was fixed at 0.3 for the hydrophilic segment—polar segment pair because this binary does not exhibit liquid-liquid separation. $\tau_{12}$ was fixed at a positive value (1.787) and $\tau_{21}$ was allowed to vary between −2 and 2. Two types of polar segments were allowed, Y− and Y+. For Y− polar segment, the values of $\tau_{12}$ and $\tau_{21}$ were (1.787, −2). For Y+ polar segment, they were (1.787, 2). Note that both Y− polar segment and Y+ polar segment exhibited the same repulsive interactions with hydrophobic segments as discussed in the previous paragraph. Also, ideal solution was assumed for Y− polar segment and Y+ polar segment mixtures (i.e., $\tau_{12}=\tau_{21}=0$).

Table 2 captures the general trends for the NRTL binary parameters that were observed for a wide variety of hydrophobic, polar, and hydrophilic molecules.

The application of the NRTL-SAC model requires a databank of molecular descriptors for common solvents used in the industry. In this example, each solvent was described by using up to four molecular descriptors, i.e., X, Y+, Y−, and Z. So, using four molecular descriptors to model a system of 60 solvents, a set of up to 4×60 molecular descriptors would be used. However, due to the fact that these molecular descriptors represent certain unique molecular characteristics, often only one or two molecular descriptors are needed for most solvents. For example, alkanes are hydrophobic and they are well represented with hydrophobicity, X, alone. Alcohols are hybrids of hydrophobic segments and hydrophilic segments and they are well represented with X and Z. Ketones, esters, and ethers are polar molecules with varying degrees of hydrophobic contents. They are well represented by X and Y's. Hence, the needed set of molecular descriptors can be much smaller than 4×60.

Determination of solvent molecular descriptors involves regression of experimental VLE or LLE data for binary systems of interested solvent and the above-mentioned reference molecules (i.e., hexane, acetonitrile, and water) or their substitutes. Solvent molecular descriptors are the adjustable parameters in the regression. If binary data is lacking for the solvent with the reference molecules, data for other binaries may be used as long as the molecular descriptors for the substitute reference molecules are already identified. In a way, these reference molecules can be thought of as molecular probes that are used to elucidate the interaction characteristics of the solvent molecules. These molecular probes express the interactions in terms of binary phase equilibrium data.

Table 3 lists the molecular descriptors identified for the common solvents in the ICH list.

TABLE 3

Molecular Descriptors for Common Solvents.

| Solvent name | X | Y− | Y+ | Z |
|---|---|---|---|---|
| ACETIC-ACID | 0.045 | 0.164 | 0.157 | 0.217 |
| ACETONE | 0.131 | 0.109 | 0.513 | |
| ACETONITRILE | 0.018 | 0.131 | 0.883 | |
| ANISOLE | 0.722 | | | |
| BENZENE | 0.607 | | 0.190 | |
| 1-BUTANOL | 0.414 | 0.007 | | 0.485 |
| 2-BUTANOL | 0.335 | 0.082 | | 0.355 |
| N-BUTYL-ACETATE | 0.317 | 0.030 | 0.330 | |
| METHYL-TERT-BUTYL-ETHER | 1.040 | 0.219 | 0.172 | |
| CARBON-TETRACHLORIDE | 0.718 | | 0.141 | |
| CHLOROBENZENE | 0.710 | | 0.424 | |
| CHLOROFORM | 0.278 | | 0.039 | |
| CUMENE | 1.208 | | 0.541 | |
| CYCLOHEXANE | 0.892 | | | |
| 1,2-DICHLOROETHANE | 0.394 | | 0.691 | |
| 1,1-DICHLOROETHYLENE | 0.529 | | 0.208 | |
| 1,2-DICHLOROETHYLENE | 0.188 | | 0.832 | |
| DICHLOROMETHANE | 0.321 | | 1.262 | |
| 1,2-DIMETHOXYETHANE | 0.081 | 0.194 | 0.858 | |
| N,N-DIMETHYLACETAMIDE | 0.067 | 0.030 | 0.157 | |
| N,N-DIMETHYLFORMAMIDE | 0.073 | 0.564 | 0.372 | |
| DIMETHYL-SULFOXIDE | 0.532 | 2.890 | | |
| 1,4-DIOXANE | 0.154 | 0.086 | 0.401 | |
| ETHANOL | 0.256 | 0.081 | | 0.507 |
| 2-ETHOXYETHANOL | 0.071 | 0.318 | | 0.237 |
| ETHYL-ACETATE | 0.322 | 0.049 | 0.421 | |
| ETHYLENE-GLYCOL | | 0.141 | | 0.338 |
| DIETHYL-ETHER | 0.448 | 0.041 | 0.165 | |
| ETHYL-FORMATE | 0.257 | | 0.280 | |
| FORMAMIDE | | 0.089 | 0.341 | 0.252 |
| FORMIC-ACID | 0.707 | 2.470 | | |
| N-HEPTANE | 1.340 | | | |
| N-HEXANE | 1.000 | | | |
| ISOBUTYL-ACETATE | 1.660 | | 0.108 | |
| ISOPROPYL-ACETATE | 0.552 | 0.154 | 0.498 | |
| METHANOL | 0.088 | 0.149 | 0.027 | 0.562 |
| 2-METHOXYETHANOL | 0.052 | 0.043 | 0.251 | 0.560 |
| METHYL-ACETATE | 0.236 | | 0.337 | |
| 3-METHYL-1-BUTANOL | 0.419 | | 0.538 | 0.314 |
| METHYL-BUTYL-KETONE | 0.673 | 0.224 | 0.469 | |
| METHYLCYCLOHEXANE | 1.162 | | 0.251 | |
| METHYL-ETHYL-KETONE | 0.247 | 0.036 | 0.480 | |
| METHYL-ISOBUTYL-KETONE | 0.673 | 0.224 | 0.469 | |
| ISOBUTANOL | 0.566 | | 0.067 | 0.485 |
| N-METHYL-2-PYRROLIDONE | 0.197 | 0.322 | | 0.305 |
| NITROMETHANE | 0.025 | | 1.216 | |
| N-PENTANE | 0.898 | | | |
| 1-PENTANOL | 0.474 | 0.223 | 0.426 | 0.248 |
| 1-PROPANOL | 0.375 | 0.030 | | 0.511 |
| ISOPROPYL-ALCOHOL | 0.351 | 0.070 | 0.003 | 0.353 |
| N-PROPYL-ACETATE | 0.514 | 0.134 | 0.587 | |
| PYRIDINE | 0.205 | 0.135 | 0.174 | |
| SULFOLANE | 0.210 | | | 0.457 |
| TETRAHYDROFURAN | 0.235 | 0.040 | 0.320 | |
| 1,2,3,4-TETRAHYDRONAPHTHALENE | 0.443 | 0.555 | | |
| TOLUENE | 0.604 | | 0.304 | |
| 1,1,1-TRICHLOROETHANE | 0.548 | | 0.287 | |
| TRICHLOROETHYLENE | 0.426 | 0.285 | | |
| M-XYLENE | 0.758 | 0.021 | 0.316 | |
| WATER | | | | 1.000 |
| TRIETHYLAMINE | 0.557 | 0.105 | | |
| 1-OCTANOL | 0.766 | 0.032 | 0.624 | 0.335 |

Among the ICH solvents, the molecular descriptors identified for anisole, cumene, 1,2-dichloroethylene, 1,2-dimethoxyethane, N,N-dimethylacetamide, dimethyl sulfoxide, ethyl formate, isobutyl acetate, isopropyl acetate, methyl-butyl-ketone, tetralin, and trichloroethylene were questionable, due to lack of sufficient experimental binary phase equilibrium data. In fact, no public data for methyl-butyl-ketone (2-hexanone) was found and its molecular descriptors were set to be the same as those for methyl-isobutyl-ketone.

Figure 4:
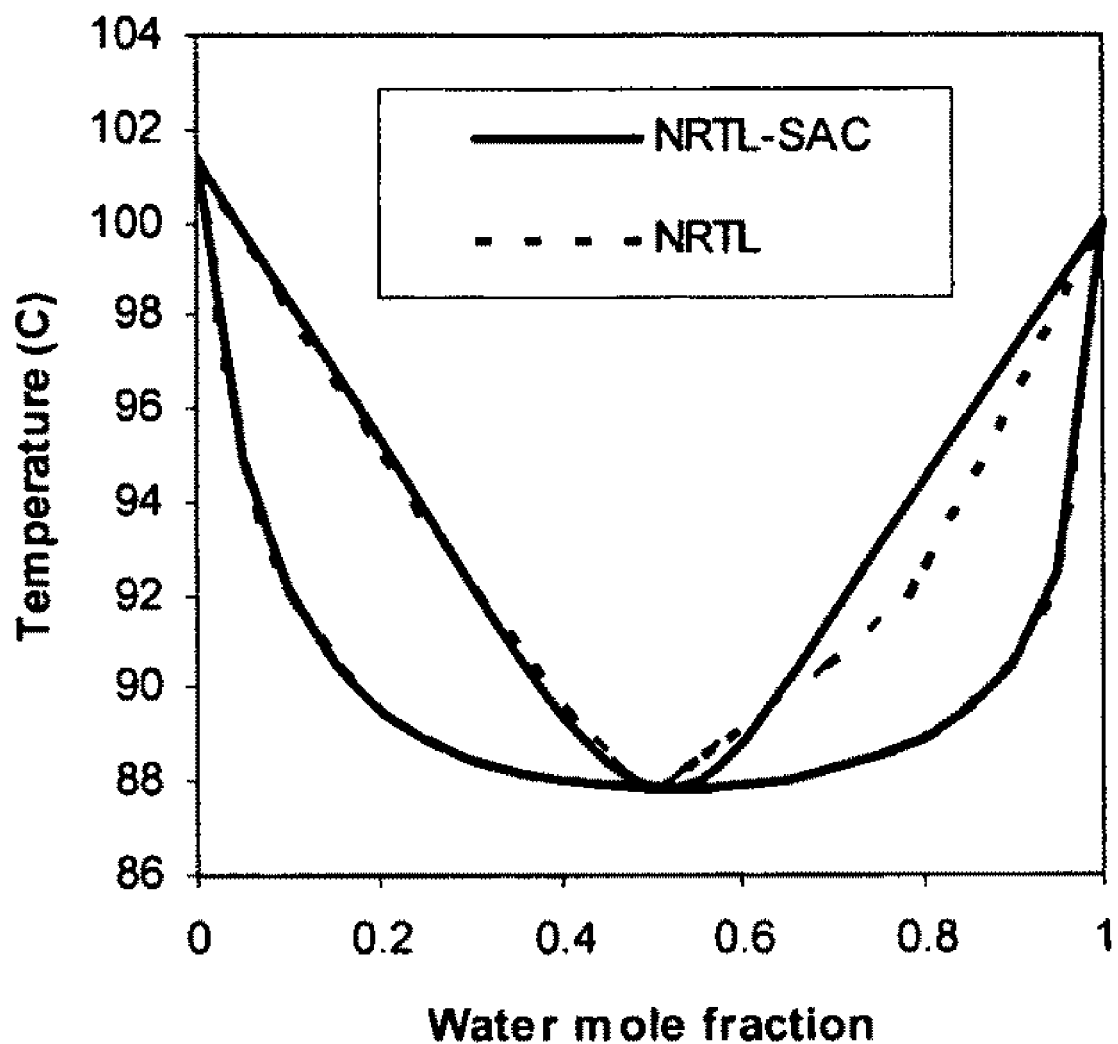
FIG. 4 illustrates a graph showing the binary phase diagram for a water, 1,4-dioxane mixture at atmospheric pressure.
Figure 5:
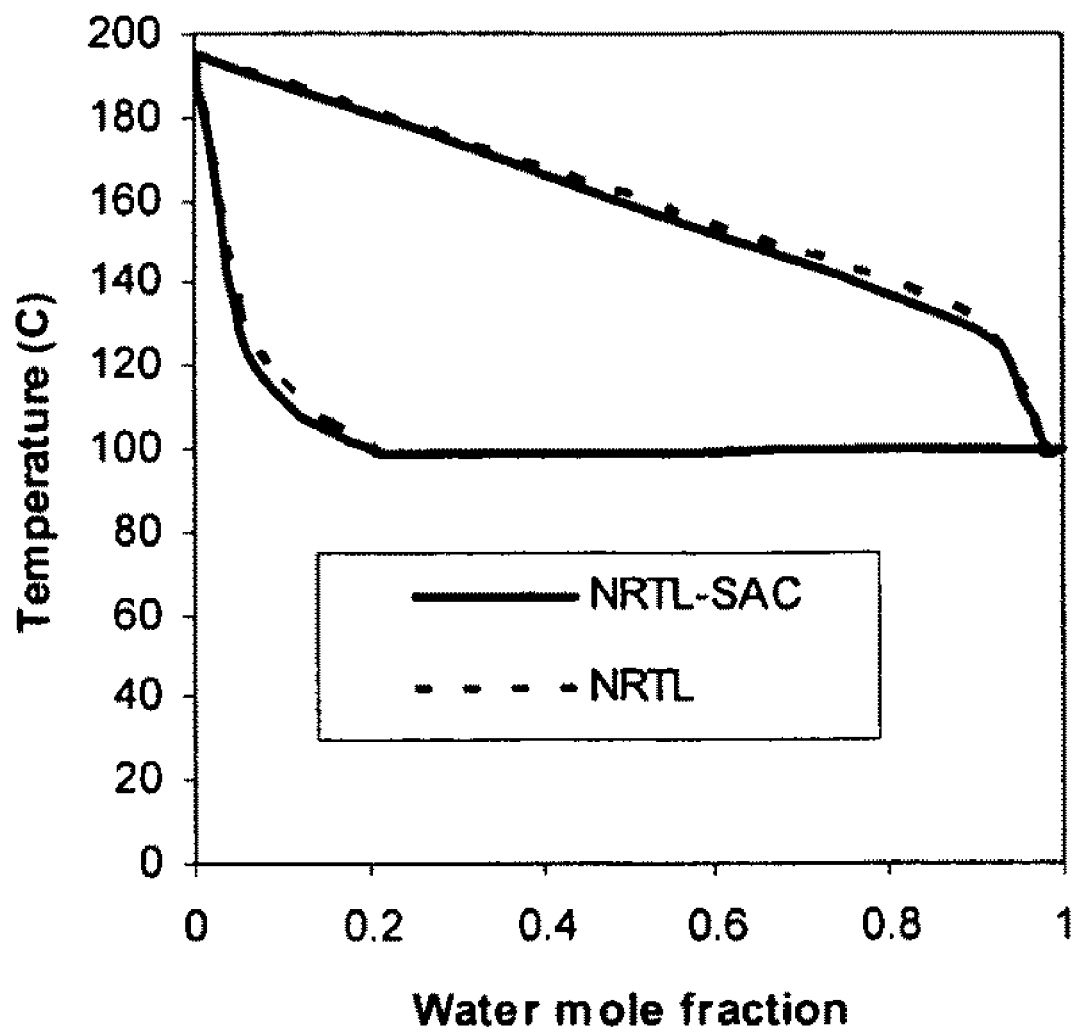
FIG. 5 illustrates a graph showing the binary phase diagram for a water, octanol mixture at atmospheric pressure.
Figure 6:
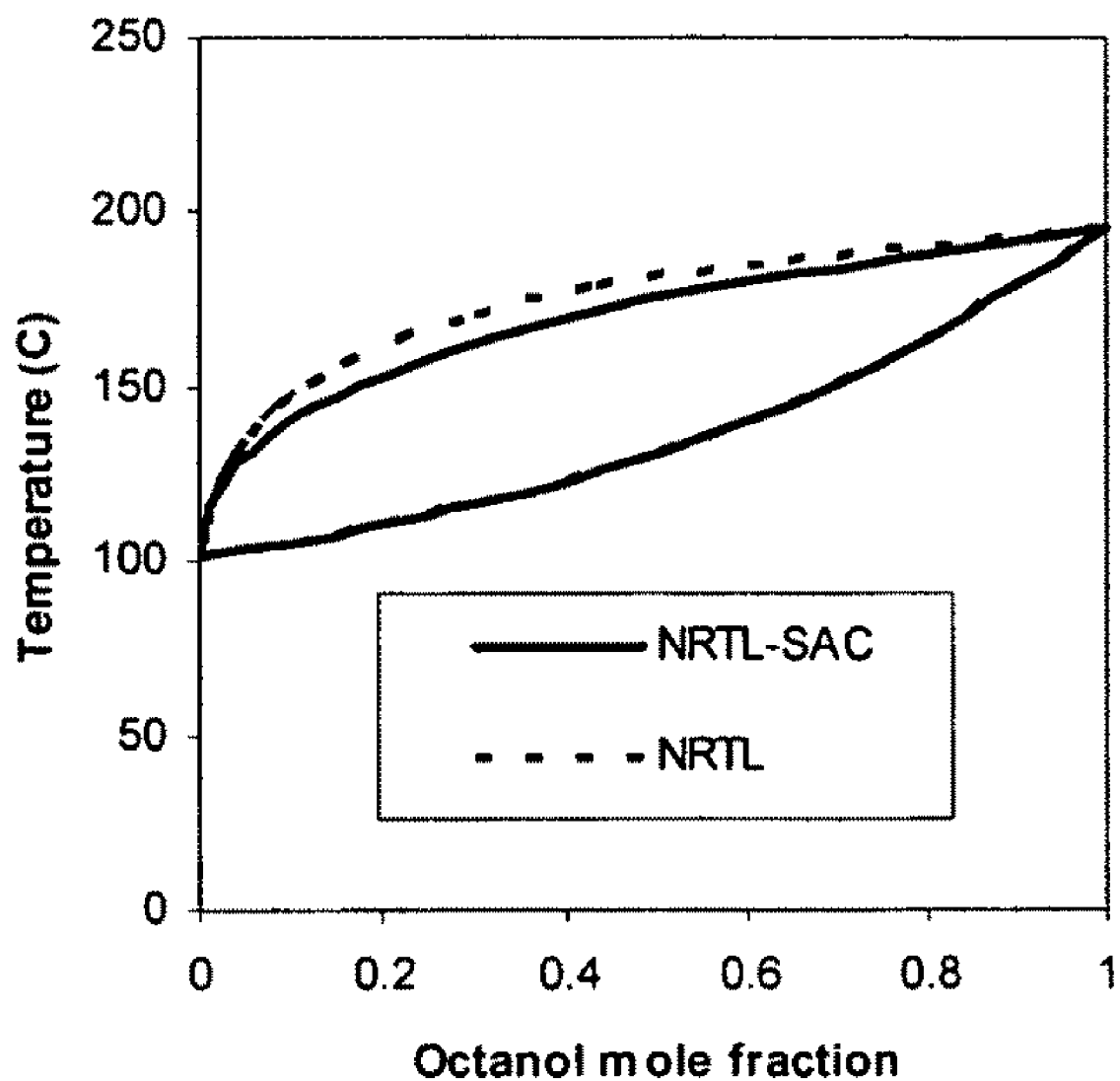
FIG. 6 illustrates a graph showing the binary phase diagram for an octanol, 1,4-dioxane mixture at atmospheric pressure.
Figure 7:
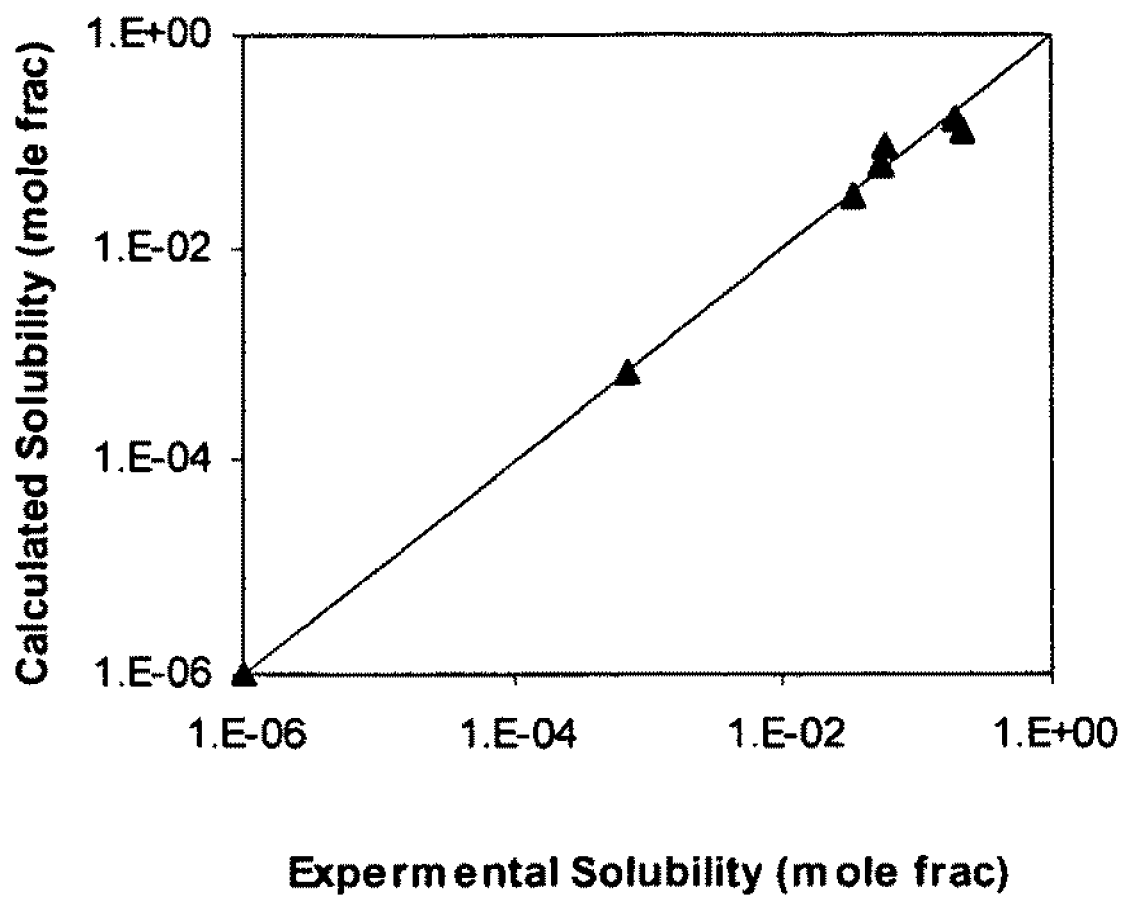
FIG. 7 illustrates a graph showing data of experimental solubilities vs. calculated solubilities for p-aminobenzoic acid in various solvents at 298.15K.
Figure 8:
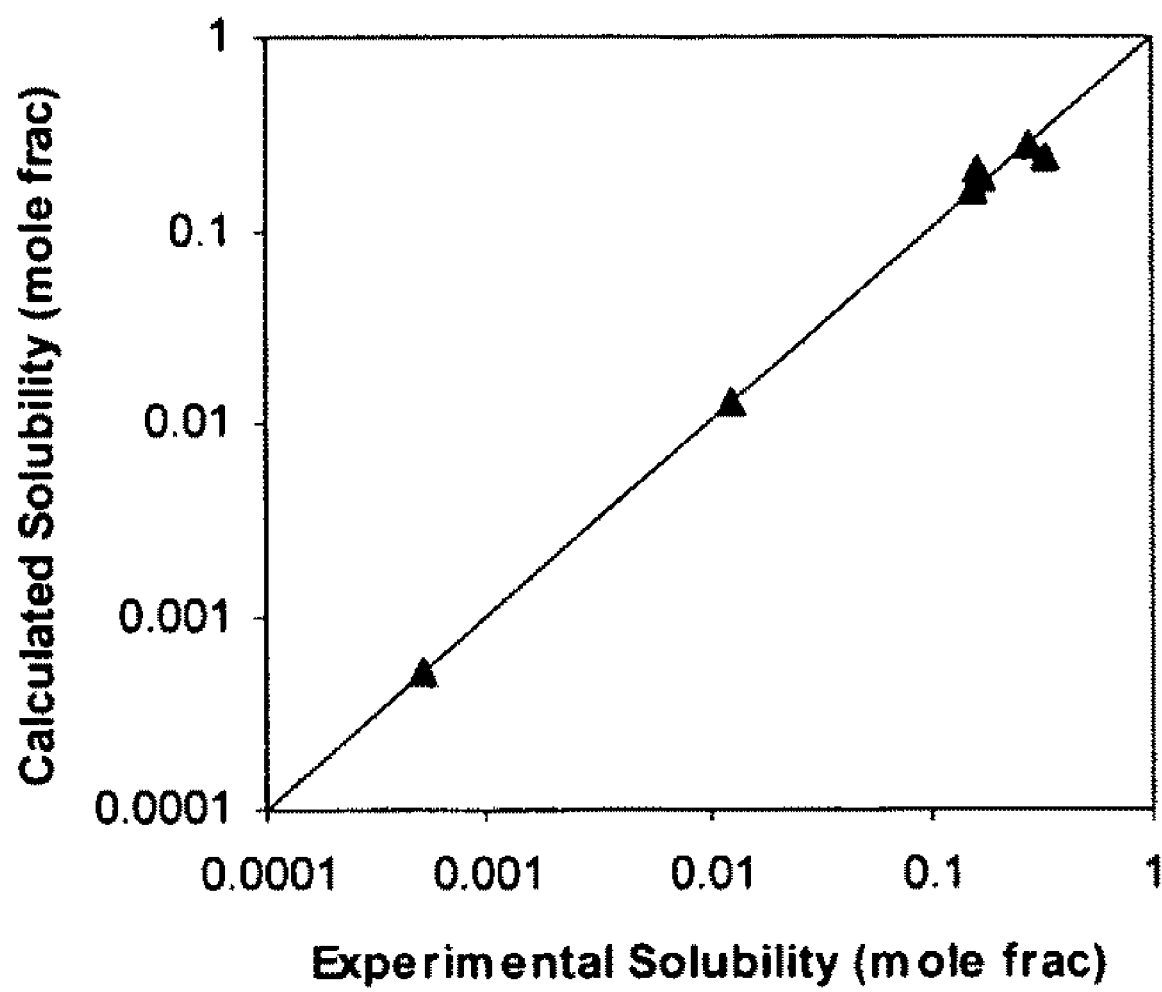
FIG. 8 illustrates a graph showing data of experimental solubilities vs. calculated solubilities for benzoic acid in various solvents at 298.15K.
Figure 9:
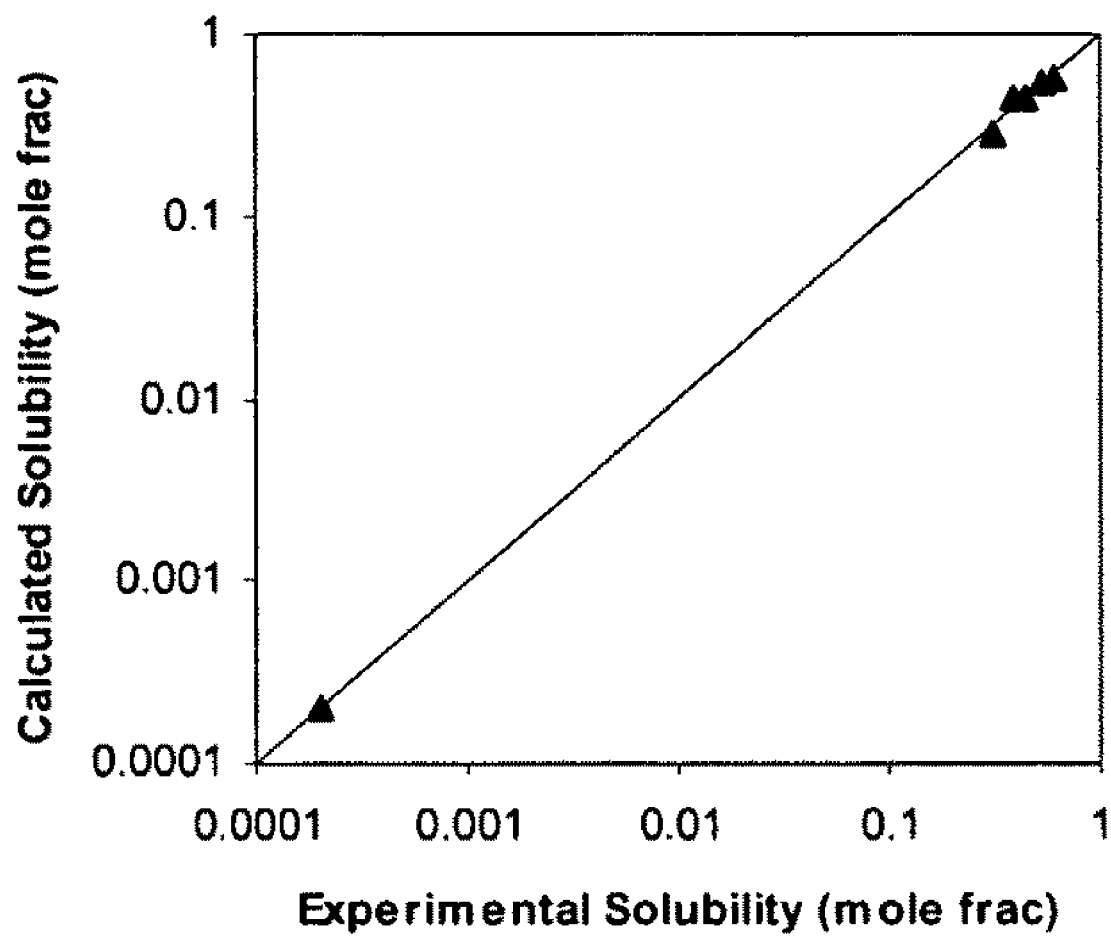
FIG. 9 illustrates a graph showing data of experimental solubilities vs. calculated solubilities for camphor in various solvents at 298.15K.
Figure 10:
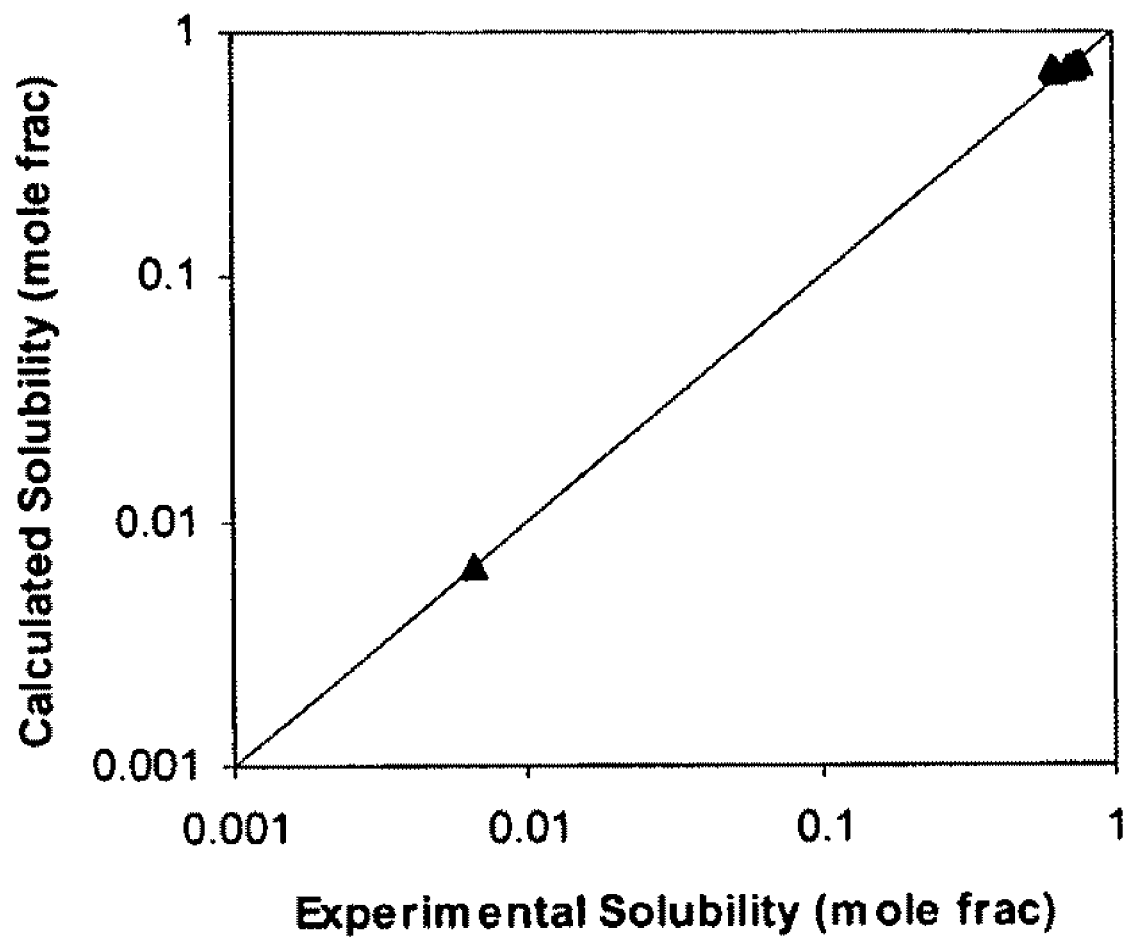
FIG. 10 illustrates a graph showing data of experimental solubilities vs. calculated solubilities for ephedrine in various solvents at 298.15K.
Figure 11:
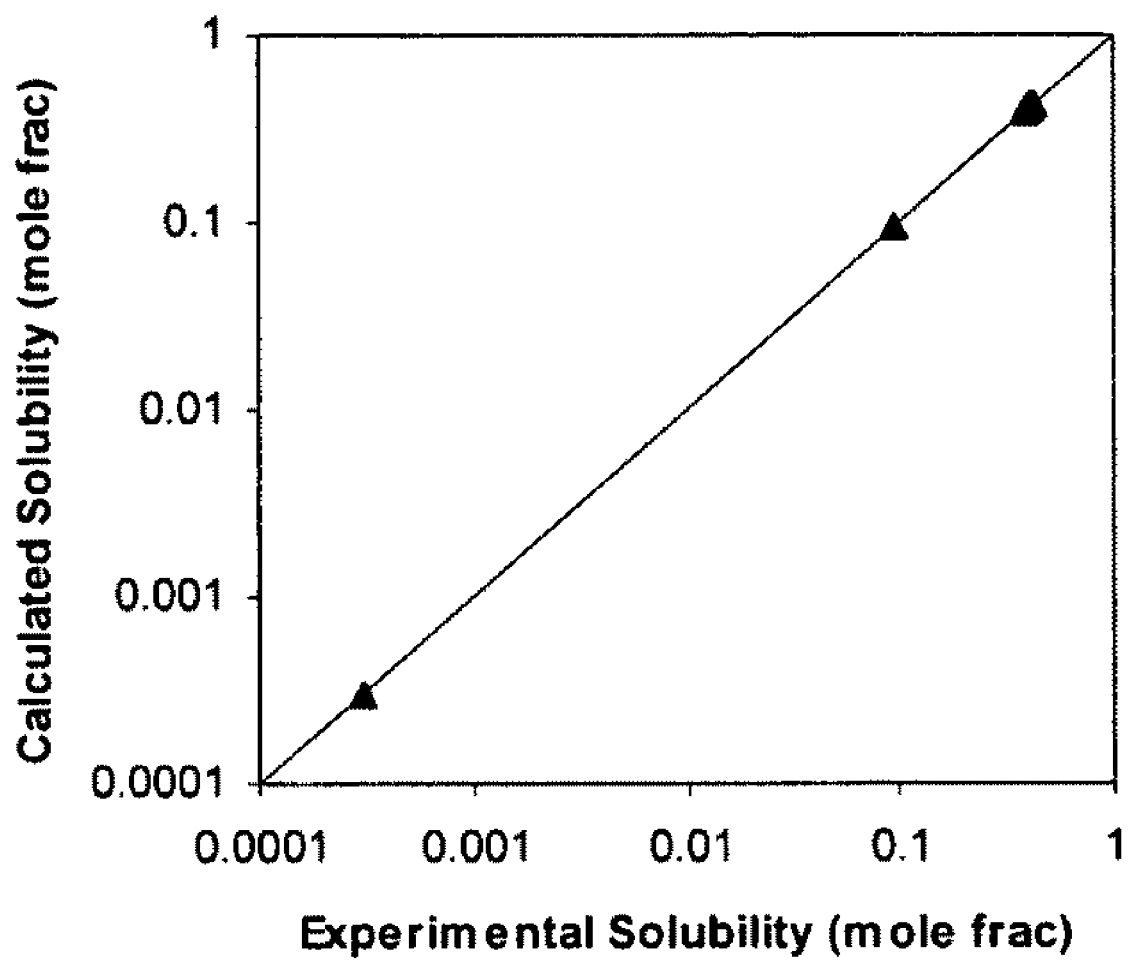
FIG. 11 illustrates a graph showing data of experimental solubilities vs. calculated solubilities for lidocaine in various solvents at 298.15K.
Figure 12:
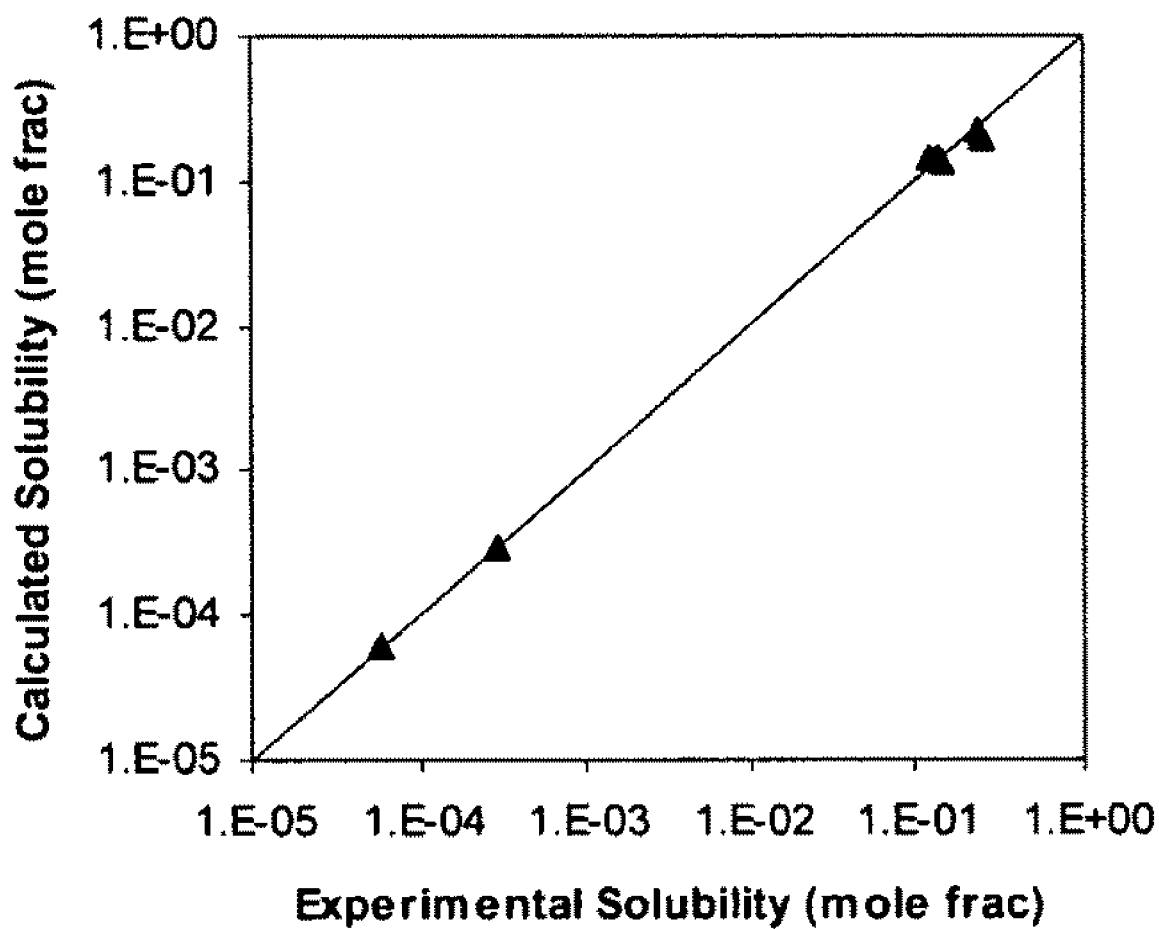
FIG. 12 illustrates a graph showing data of experimental solubilities vs. calculated solubilities for methylparaben in various solvents at 298.15K.
Figure 13:
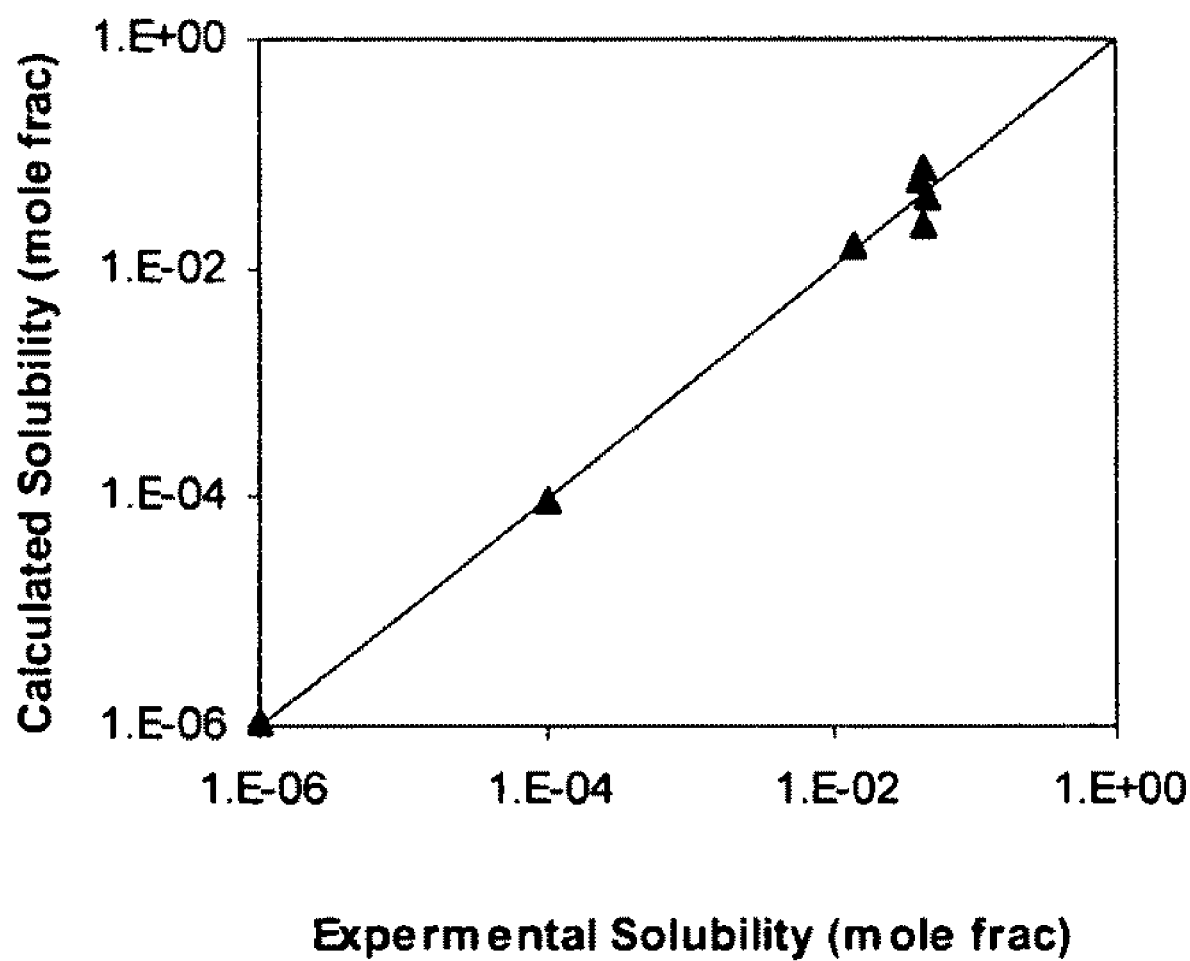
FIG. 13 illustrates a graph showing data of experimental solubilities vs. calculated solubilities for testosterone in various solvents at 298.15K.
Figure 14:
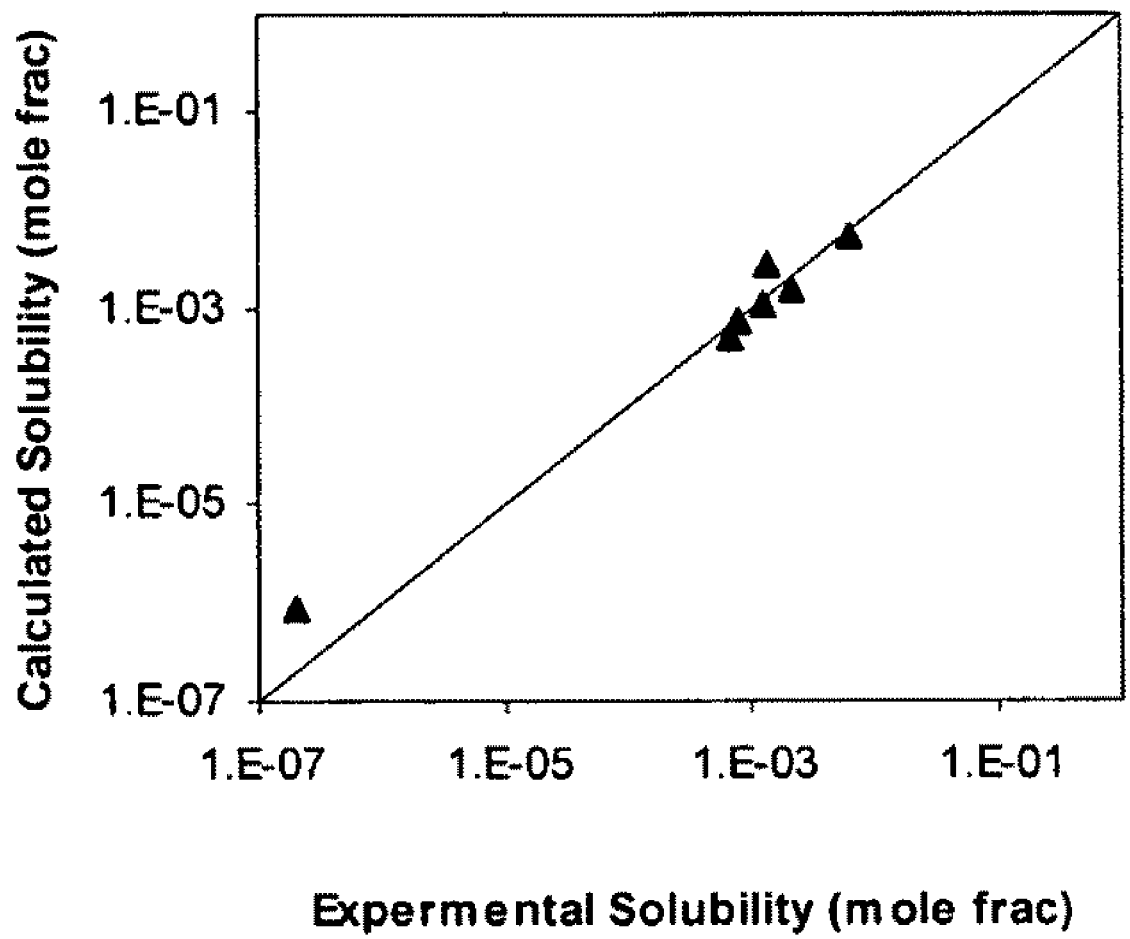
FIG. 14 illustrates a graph showing data of experimental solubilities vs. calculated solubilities for theophylline in various solvents at 298.15K.

The NRTL-SAC model with the molecular descriptors qualitatively captures the interaction characteristics of the solvent mixtures and the resulting phase equilibrium behavior. FIGS. 4 to 6 contain three graphs illustrating the binary phase diagrams for a water, 1,4-dioxane, and octanol system at atmospheric pressure. The graphs illustrate the predictions of both the NRTL model with the binary parameters in Table 1 and NRTL-SAC models with the model descriptors of Table 3. FIG. 4 illustrates the water, 1,4-dioxane mixture; FIG. 5 illustrates the water, octanol mixture; and FIG. 6 illustrates the octanol, 1,4-dioxane mixture. The predictions with the NRTL-SAC model are broadly consistent with the calculations from the NRTL model that are generally understood to represent experimental data within engineering accuracy.

Example 2

Model Prediction Results

Data compiled by Marrero and Abildskov provides a good source of solubility data for large, complex chemicals. Marrero, J. & Abildskov, J., *Solubility and Related Properties of Large Complex Chemicals, Part 1: Organic Solutes Ranging from $C_4$ to $C_{40}$*, CHEMISTRY DATA SERIES XV, DECHEMA, (2003). From that applicants extracted solubility data for the 8 molecules reported by Lin and Nash. Lin, H.-M. & R. A. Nash, *An Experimental Method for Determining the Hildebrand Solubility Parameter of Organic Electrolytes*, 82 J. PHARMACEUTICAL SCI. 1018 (1993). Also tested, were 6 additional molecules with sizable solubility data sets.

The NRTL-SAC model was applied to the solvents that are included in Table 3. The molecular descriptors determined for the solutes are summarized in Table 4. During the data regression, all experimental solubility data, regardless of the order of magnitude, were assigned with a standard deviation of 20%. The comparisons between the experimental solubility and the calculated solubility are given in FIGS. 7 to 20, which illustrate phase diagrams for the systems at 298.15K and atmospheric pressure.

Good representations for the solubility data was obtained with the NRTL-SAC model. The RMS errors in ln x for the fits are given in Table 4.

$K_{sp}$, the solubility product constant, corresponds to the ideal solubility (in mole fraction) for the solute. The quality of the fit reflects both the effectiveness of the NRTL-SAC model and the quality of the molecular descriptors identified from the limited available experimental data for the solvents.

FIGS. 7, 8, 9, 10, 11, 12, 13, and 14 include graphs illustrating the experimental solubilities vs. calculated solubilities for p-aminobenzoic acid, benzoic acid, camphor, ephedrine, lidocaine, methylparaben, testosterone, and theophylline, respectively, in various solvents at 298.15K. The various solvents used were selected from a group of 33 solvents, including acetic acid, acetone, benzene, 1-butanol, n-butyl acetate, carbon tetrachloride, chlorobenzene, chloroform, cyclohexane, 1,2-dichloroethane, dichloromethane, 1,2-dimethoxyethane, N,N-dimethylformamide, dimethyl-sulfoxide, 1,4-dioxane, ethanol, 2-ethoxyethanol, ethyl acetate, ethylene glycol, diethyl ether, formamide, n-heptane, n-hexane, isopropyl acetate, methanol, methyl acetate, 1-pentanol, 1-propanol, isopropyl alcohol, teterhydrofuran tetrahydrofuran, toluene, water, and 1-octanol. The experimental solubility data was represented well with the NRTL-SAC model.

Figure 15:
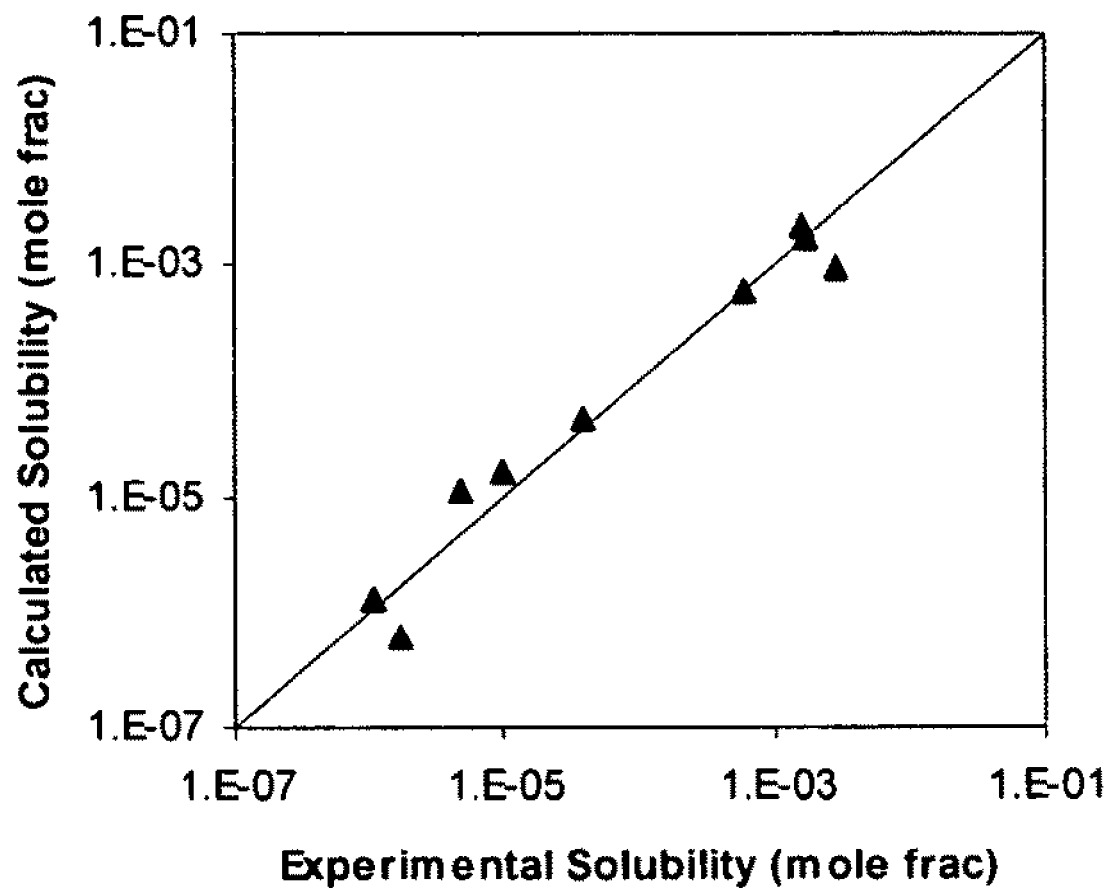
FIG. 15 illustrates a graph showing data of experimental solubilities vs. calculated solubilities for estriol in nine solvents at 298.15K.

FIG. 15 includes a graph illustrating the experimental solubilities vs. calculated solubilities for estriol in 9 solvents at 298.15K. The experimental solubility data was represented well with the NRTL-SAC model. The data for tetrahydrofuran is found to be a very significant outlier and it is not included in the 9 solvents shown in FIG. 15.

Figure 16:
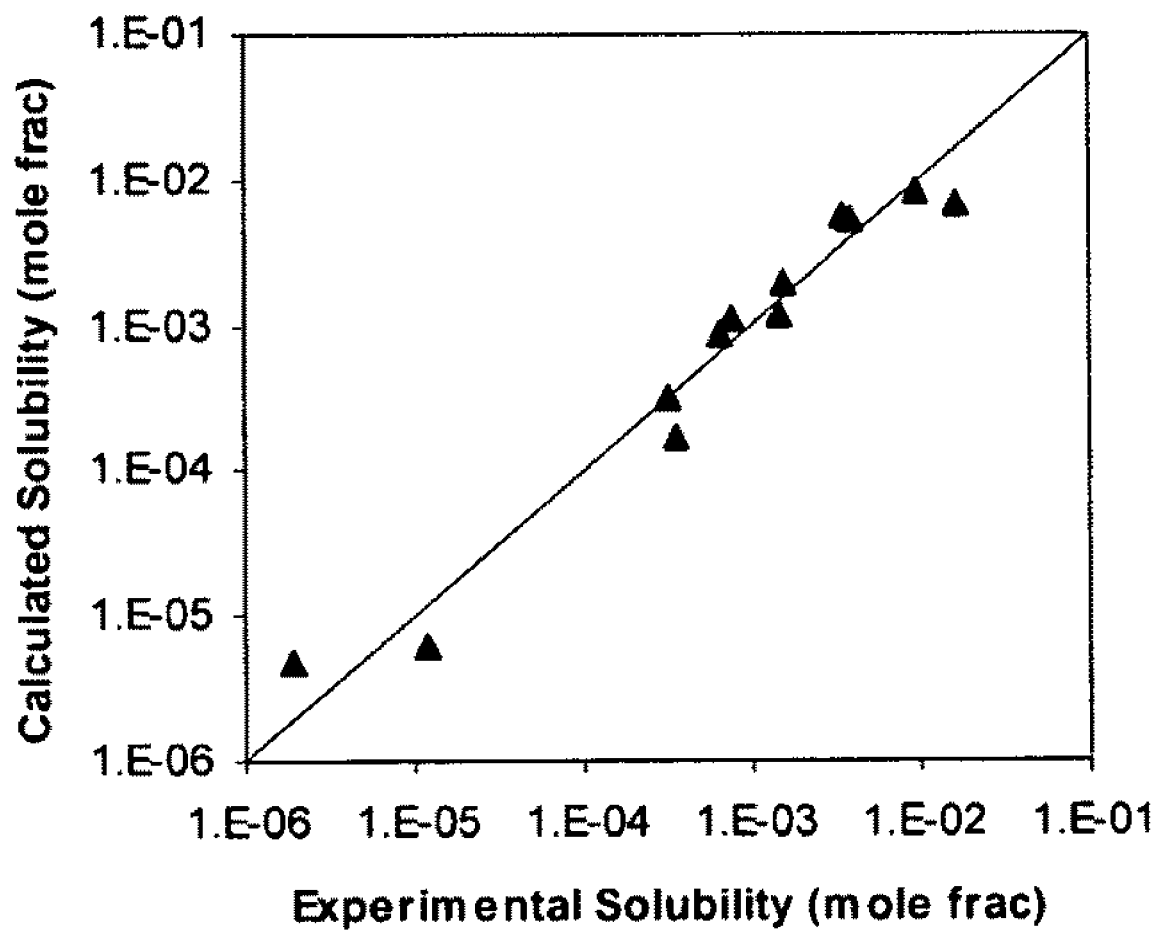
FIG. 16 illustrates a graph showing data of experimental solubilities vs. calculated solubilities for estrone in various solvents at 298.15K.

FIG. 16 includes a graph illustrating the experimental solubilities vs. calculated solubilities for estrone in various solvents at 298.15K. The experimental solubility data was represented well with the NRTL-SAC model.

Figure 17:
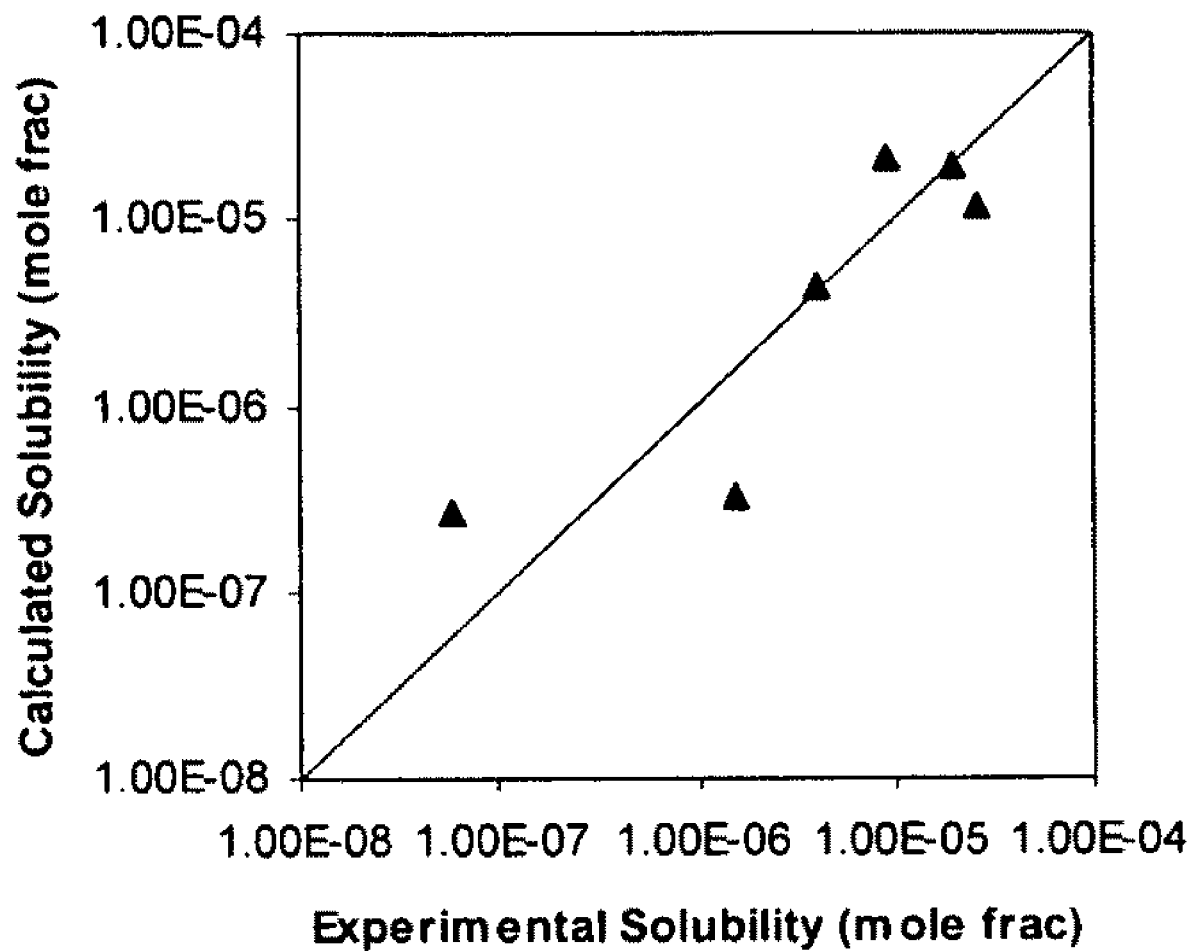
FIG. 17 illustrates a graph showing data of experimental solubilities vs. calculated solubilities for morphine in six solvents at 308.15K.

FIG. 17 includes a graph illustrating the experimental solubilities vs. calculated solubilities for morphine in 6 solvents at 308.15K. Cyclohexane and hexane were outliers. They are very low solubility solvents for morphine and the quality of the data is possibly subject to larger uncertainties.

Figure 18:
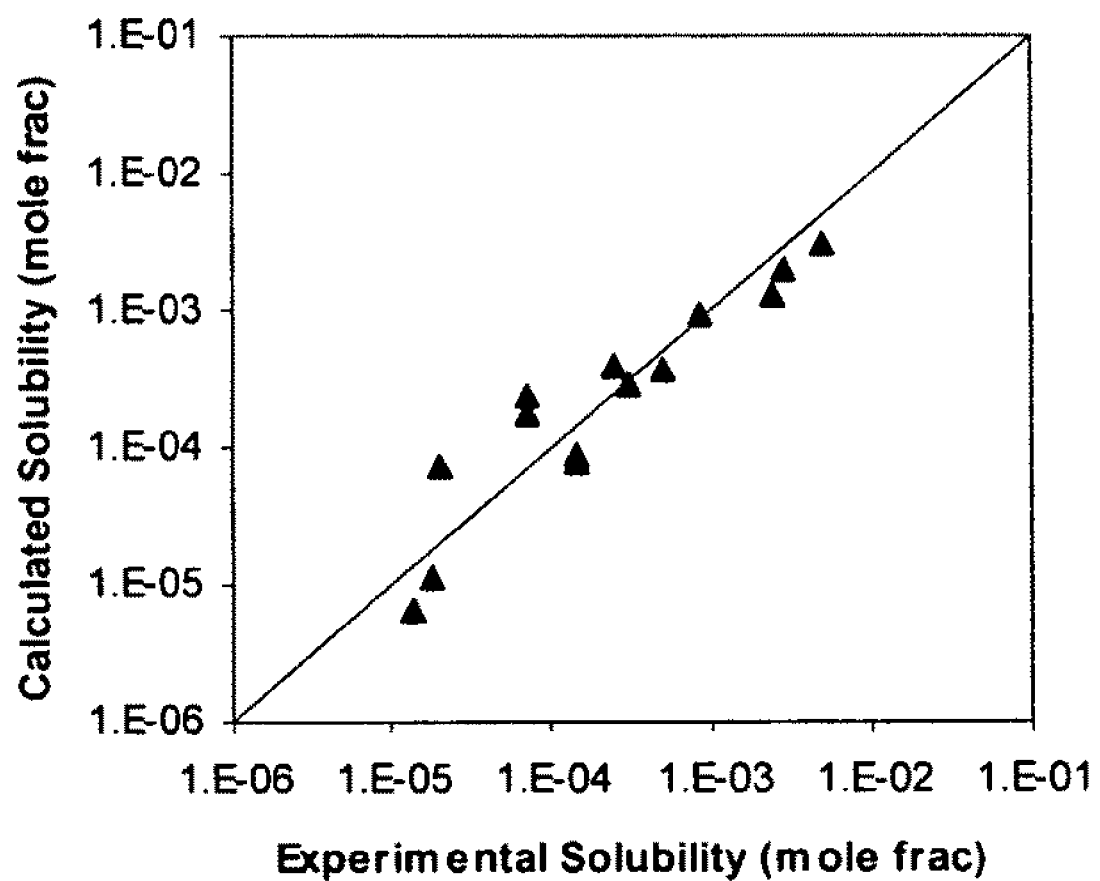
FIG. 18 illustrates a graph showing data of experimental solubilities vs. calculated solubilities for piroxicam in 14 solvents at 298.15K.

FIG. 18 illustrates a graph of the experimental solubilities vs. calculated solubilities for piroxicam in 14 solvents at 298.15K. 1,2-dichloroethane, chloroform, diethyl ether, and N,N-dimethylformamide (DMF) were found to be major outliers and are not included in the 14 solvents shown in FIG. 18.

TABLE 4

Molecular descriptors for solutes.

| Solute | MW | # of solvents | T (K) | X | Y- | Y+ | Z | $lnK_{sp}$ | RMS error on ln x |
|---|---|---|---|---|---|---|---|---|---|
| p-Aminobenzoic acid | 137.14 | 7 | 298.15 | 0.218 | 0.681 | 1.935 | 0.760 | −2.861 | 0.284 |
| Benzoic acid | 122.12 | 7 | 298.15 | 0.524 | 0.089 | 0.450 | 0.405 | −1.540 | 0.160 |
| Camphor | 152.23 | 7 | 298.15 | 0.604 | 0.124 | 0.478 | 0.000 | −0.593 | 0.092 |
| Ephedrine | 165.23 | 7 | 298.15 | 0.458 | 0.068 | 0.000 | 0.193 | −0.296 | 0.067 |
| Lidocaine | 234.33 | 7 | 298.15 | 0.698 | 0.596 | 0.293 | 0.172 | −0.978 | 0.027 |
| Methylparaben | 152.14 | 7 | 298.15 | 0.479 | 0.484 | 1.218 | 0.683 | −2.103 | 0.120 |
| Testosterone | 288.41 | 7 | 298.15 | 1.051 | 0.771 | 0.233 | 0.669 | −3.797 | 0.334 |
| Theophylline | 180.18 | 7 | 298.15 | 0.000 | 0.000 | 0.757 | 1.208 | 0.341 | −6.110 | 0.661 |
| Estriol | 288.38 | 9[a] | 298.15 | 0.853 | 0.000 | 0.291 | 1.928 | −7.652 | 0.608 |
| Estrone | 270.37 | 12 | 298.15 | 0.499 | 0.679 | 1.521 | 0.196 | −6.531 | 0.519 |
| Morphine | 285.34 | 6 | 308.15 | 0.773 | 0.000 | 0.000 | 1.811 | −4.658 | 1.007 |
| Piroxicam | 331.35 | 14[b] | 298.15 | 0.665 | 0.000 | 1.803 | 0.169 | −7.656 | 0.665 |
| Hydrocortisone | 362.46 | 11[c] | 298.15 | 0.401 | 0.970 | 1.248 | 0.611 | −6.697 | 0.334 |
| Haloperidol | 375.86 | 13[d] | 298.15 | 0.827 | 0.000 | 0.000 | 0.131 | −4.398 | 0.311 |

[a]With THF excluded.
[b]With 1,2 dichloroethane, chloroform, diethyl ether, and DMF excluded.
[c]With hexane excluded.
[d]With chloroform and DMF excluded.

Interestingly, Bustamante, et al. also reported 1,2-dichloroethane, chloroform, and diethyl ether as outliers in their study based on solubility parameter models. P. Bustamante, et al., *Partial Solubility Parameters of Piroxicam and Niflumic Acid*, 1998 INT. J. OF PHARM. 174, 141.

Figure 19:
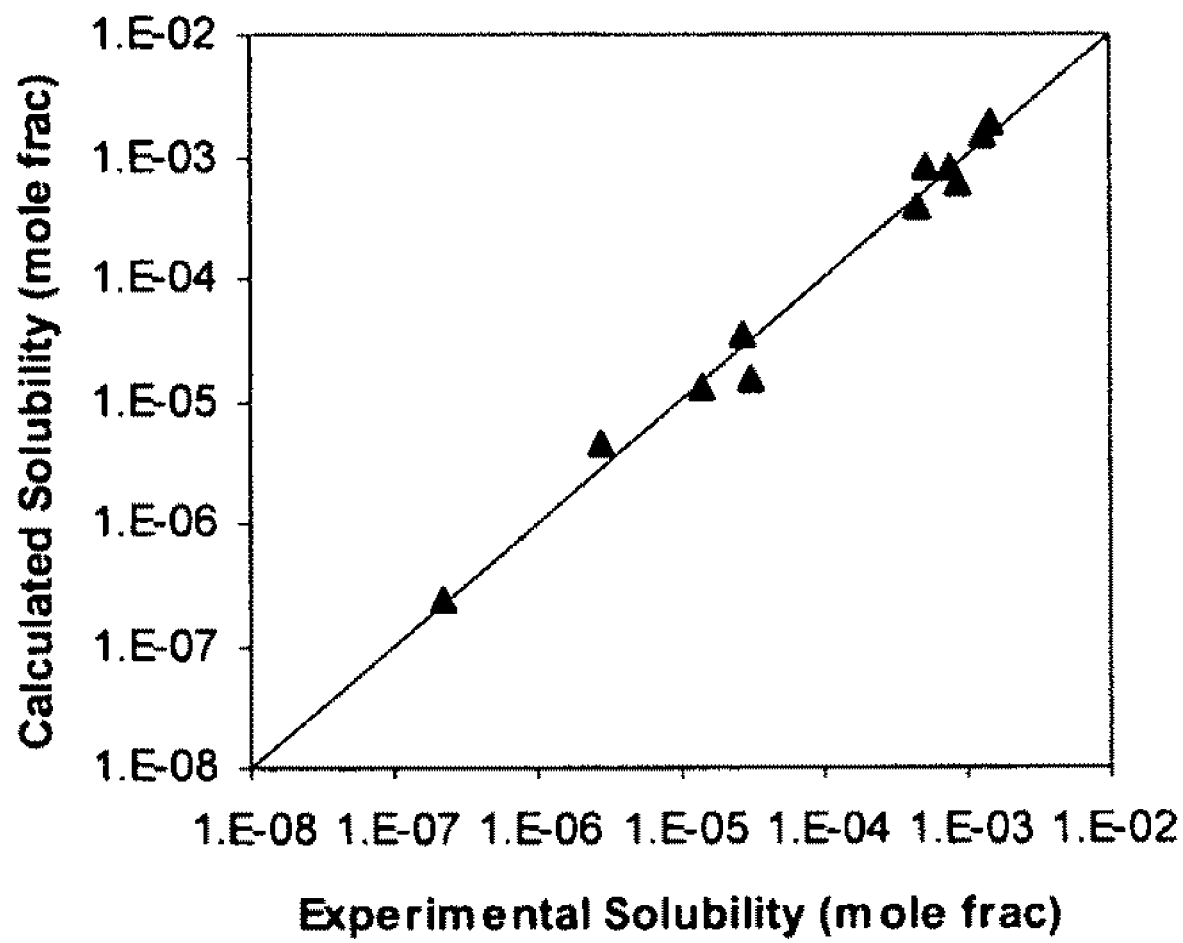
FIG. 19 illustrates a graph showing data of experimental solubilities vs. calculated solubilities for hydrocortisone in 11 solvents at 298.15K.

FIG. 19 illustrates a graph of the experimental solubilities vs. calculated solubilities for hydrocortisone in 11 solvents at 298.15K. Hexane is excluded because of the extreme low solubility of hydrocortisone in hexane which could possibly subject the data to larger uncertainty.

Figure 20:
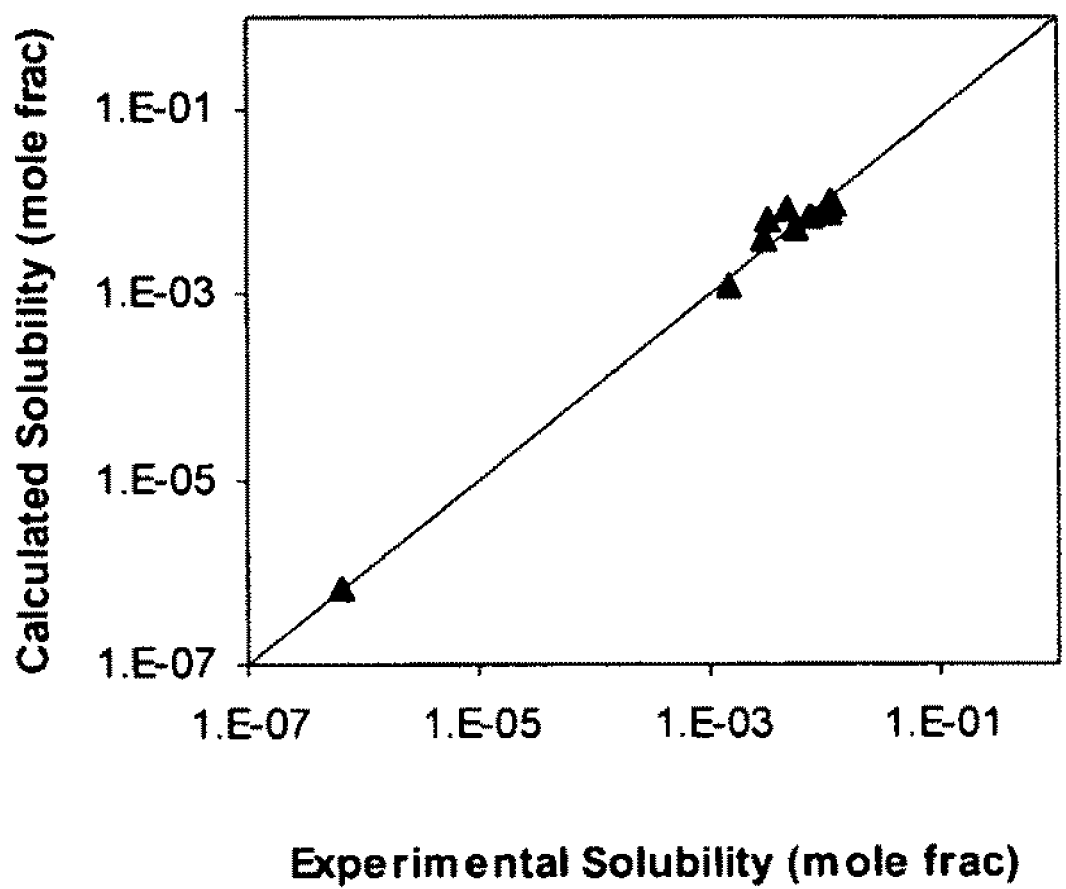
FIG. 20 illustrates a graph showing data of experimental solubilities vs. calculated solubilities for haloperidol in 13 solvents at 298.15K.

FIG. 20 illustrates a graph of the experimental solubilities vs. calculated solubilities for haloperidol in 13 solvents at 298.15K. Haloperidol showed unusually high solubilities in chloroform and DMF and these two solvents are not included in the 13 solvents.

The average RMS error on ln x for the predictions vs. experimental solubility data in Table 4 is 0.37. This corresponds to about ±45% accuracy in solubility predictions.

Experiment 3

Comparison of NRTL-SAC Model to Prior Art Methods for Pharmaceutical Components

The solubilities of various pharmaceutical compounds was modeled with the NRTL-SAC approach of the present invention as well as some prior art models (e.g., the Hanson model and the UNIFAC model) to compare their relative accuracies. The pharmaceutical compounds used included VIOXX®, ARCOXIA®, Lovastatin, Simvastatin, FOSAMAX®. (Available from Merck & Co., Inc., Whitehouse Station, N.J.). The solvents used included water, N,N-Dimethylformamide ("DMF"), 1-propanol, 2-propanol, 1-butanol, toluene, Chloro-benzene, acetonitrile, ethyl acetate, methanol, ethanol, heptane, acetone, and triethylamine (TEA).

Saturated solutions of the compounds in the solvents were allowed to equilibrate for at least 48 hours. Supernatant fluid was filtered and diluted, and an a high pressure liquid chromatography (HPLC) concentration analysis was performed to compare the predicted solubility values with actual solubility values.

The NRTL-SAC model of the present invention gave a RMS error on ln x of about 0.5 (i.e., an accuracy and predictive capability of ±~50%), while the Hansen model had a RMS error on ln x of more than 0.75 and the UNIFAC model had a RMS error on ln x of more than 1.75. Additional comparisons were made for dual-solvent/pharmaceutical systems, and acceptable predictions were obtained from the NRTL-SAC model of the present invention.

These experiments show that the NRTL-SAC model is a simple correlative activity coefficient equation that requires only component-specific molecular descriptors (i.e., conceptual segments). Conceptually, the approach suggests that a practitioner account for the liquid ideality of both small solvent molecules and complex pharmaceutical molecules in terms of component-specific molecular descriptors (e.g., hydrophobicity, polarity, and hydrophilicity). In practice, these molecular descriptors become the adjustable parameters that are determined from selected experimental data. With the development of molecular descriptors for solvents and organic solutes, engineering calculations can be performed for various phase equilibrium studies, including solubilities in solvents and solvent mixtures for solvent selection. The NRTL-SAC model provides good qualitative representation on phase behaviors of organic solvents and their complex pharmaceutical solutes and it offers a practical predictive methodology for use in pharmaceutical process design.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of modeling solubility of a pharmaceutical component in a mixture that includes at least one pharmaceutical component and at least one solvent using a modeler, the method comprising the computer implemented steps of:
    a) providing a computer programmed to serve as a modeler, the modeler during execution being formed of (i) a databank of molecular descriptors of known pharmaceutical components and known solvents, and (ii) a calculator of molecular descriptors of unknown pharmaceutical components and unknown solvents, the modeler being configured to be executable by a processor;
    b) determining at least one conceptual segment, instead of a molecular structural segment, for the at least one pharmaceutical component, including for each conceptual segment, (i) identifying the conceptual segment as one of a hydrophobic segment, a hydrophilic segment, a polar segment, or a combination thereof, and (ii) defining a segment number for the conceptual segment, the segment number being based on experimental data and being one of carried in the databank of molecular descriptors of known pharmaceutical components or obtained using the calculator of molecular descriptors of unknown pharmaceutical components by best fit of experimental phase equilibrium data for binary systems of unknown pharmaceutical components and reference pharmaceutical components;
    c) determining at least one conceptual segment, instead of a molecular structural segment, for the at least one solvent, including for each conceptual segment, (i) identifying the conceptual segment as one of a hydrophobic segment, a hydrophilic segment, a polar segment, or a combination thereof, and (ii) defining a segment number for the conceptual segment, the segment number being based on experimental data and being one of carried in the databank of molecular descriptors of known solvents or obtained using the calculator of molecular descriptors of unknown solvents;
    d) providing the determined at least one conceptual segment to the modeler, and in response the modeler using the determined at least one conceptual segment for the at least one pharmaceutical component and the determined at least one conceptual segment for the at least one solvent, to compute solubility of the at least one pharmaceutical component in the mixture,
        the modeler computing the solubility by determining an activity coefficient of the at least one pharmaceutical component, the activity coefficient being formed of at least a local composition interaction contribution to the activity coefficient of the at least one pharmaceutical component based on the determined at least one conceptual segment;
    e) analyzing the computed solubility, said analyzing being by the modeler and resulting in the modeler forming a solubility model of the at least one pharmaceutical component in the mixture; and
    f) outputting the formed solubility model from the modeler to a computer display monitor.

2. The method of claim 1, wherein the at least one pharmaceutical component has a gram molecular weight in the range of between about 100 daltons and about 900 daltons.

3. The method of claim 1, wherein the at least one pharmaceutical component has a gram molecular weight in the range of between about 200 daltons and about 600 daltons.

4. The method of claim 1, wherein the at least one pharmaceutical component is a nonelectrolytic compound.

5. The method of claim 1, wherein the at least one pharmaceutical component is a nonpolymeric compound.

6. The method of claim 1, wherein the at least one pharmaceutical component is at least one compound selected from the group consisting of an organic salt, an organic nonelectrolyte, a compound possessing a net charge, and a zwitterion.

7. The method of claim 1, wherein at least two conceptual segments for the at least one pharmaceutical component are determined.

8. The method of claim 1, wherein at least two conceptual segments for the at least one solvent are determined.

9. The method of claim 1, wherein the mixture includes any number or combination of liquid, solid and vapor phases.

10. The method of claim 1, wherein the mixture includes at least one liquid phase.

11. The method of claim 1, wherein the mixture includes at least one liquid phase and at least one solid phase.

12. The method of claim 1, wherein the mixture includes at least two liquid solvents.

13. The method of claim 1, wherein at least a portion of the at least one pharmaceutical component is in a solid phase and the step of computing solubility includes calculating:

$$\ln x_I^{SAT} = \frac{\Delta_{fus} S}{R}\left(1 - \frac{T_m}{T}\right) - \ln \gamma_I^{SAT},$$

wherein:
T is a temperature of the mixture;
$T_m$ is the melting temperature of the at least one pharmaceutical component,
T is less than or equal to $T_m$;
$x_I^{SAT}$ is the mole fraction of the at least one pharmaceutical component dissolved in the at least one solvent at saturation;
$\Delta_{fus} S$ is the entropy of fusion of the at least one pharmaceutical component;
$\gamma_I^{SAT}$ is the activity coefficient, $\gamma_I$, for the at least one pharmaceutical component in the at least one solvent at saturation; and
R is the gas constant.

14. The method of claim 13, wherein the step of computing solubility further includes determining $\gamma_I$, wherein $$\ln \gamma_I = \ln \gamma_I^C + \ln \gamma_I^R,$$

$\gamma_I$ is an activity coefficient for the at least one pharmaceutical component of the mixture;
$\gamma_I^C$ is a combinatorial contribution to the activity coefficient for the at least one pharmaceutical component of the mixture; and
$\gamma_I^R$ is a residual contribution to the activity coefficient of the at least one pharmaceutical component.

15. The method of claim 14, wherein the step of computing solubility further includes computing $$\ln \gamma_I^R = \ln \gamma_I^{lc} = \sum_m r_{m,I} [\ln \gamma_m^{lc} - \ln \gamma_m^{lc,I}],$$

$$\ln \gamma_m^{lc} = \frac{\sum_j x_j G_{jm} \tau_{jm}}{\sum_k x_k G_{km}} + \sum_{m'} \frac{x_{m'} G_{mm'}}{\sum_k x_k G_{km'}} \left(\tau_{mm'} - \frac{\sum_k x_k G_{km'} \tau_{km'}}{\sum_k x_k G_{km'}}\right);$$

$$\ln \gamma_m^{lc,I} = \frac{\sum_j x_{j,I} G_{jm} \tau_{jm}}{\sum_k x_{k,I} G_{km}} + \sum_{m'} \frac{x_{m',I} G_{mm'}}{\sum_k x_{k,I} G_{km'}} \left(\tau_{mm'} - \frac{\sum_k x_{k,I} G_{km'} \tau_{km'}}{\sum_k x_{k,I} G_{km'}}\right);$$

$$x_j = \frac{\sum_J x_J r_{j,J}}{\sum_I \sum_i x_I r_{i,I}}; \text{ and}$$

$$x_{j,I} = \frac{r_{j,I}}{\sum_j r_{j,I}};$$

wherein:
i, j, k, m, and m' are conceptual segment species; I and J are pharmaceutical components;
$x_j$ is a conceptual segment mole fraction of conceptual segment species j;
$x_J$ is a mole fraction of J;
$r_{m,I}$ is the equivalent number of conceptual segment species m contained in I,
$\gamma_m^{lc}$ is an activity coefficient of conceptual segment species m, and
$\gamma_m^{lc,I}$ is an activity coefficient of conceptual segment species m contained only in I;
G and τ are local binary quantities related to each other by a non-random factor parameter α; and $G = \exp(-\alpha \tau)$.

* * * * *